US006994958B2

(12) United States Patent (10) Patent No.: US 6,994,958 B2
Arguello et al. (45) Date of Patent: Feb. 7, 2006

(54) METHODS FOR SEPARATING AND/OR IDENTIFYING DNA MOLECULES

(75) Inventors: Rafael Arguello, London (GB); Alejandro Madrigal, London (GB)

(73) Assignee: Anthony Nolan Bone Marrow Trust (GB)

( * ) Notice: Subject to any disclaimer, the term of this patent is extended or adjusted under 35 U.S.C. 154(b) by 779 days.

(21) Appl. No.: 09/077,615

(22) PCT Filed: Nov. 29, 1996

(86) PCT No.: PCT/GB96/02960

§ 371 (c)(1),
(2), (4) Date: Oct. 23, 1998

(87) PCT Pub. No.: WO97/20070

PCT Pub. Date: Jun. 5, 1997

(65) Prior Publication Data

US 2003/0104363 A1 Jun. 5, 2003

(30) Foreign Application Priority Data

Nov. 29, 1995 (GB) .............................. 9524379
Jan. 8, 1996 (GB) .............................. 9600304
May 10, 1996 (GB) .............................. 9609823

(51) Int. Cl.
*C12Q 1/68* (2006.01)

(52) U.S. Cl. ......................... 435/6; 438/91.2
(58) Field of Classification Search ............. 435/6, 435/91.2; 536/24.3; 204/450
See application file for complete search history.

(56) References Cited

U.S. PATENT DOCUMENTS 5,387,505 A * 2/1995 Wu ................................ 435/6
5,468,611 A 11/1995 Baxter-Lowe
5,597,910 A * 1/1997 Gudibande et al. ......... 536/23.4

FOREIGN PATENT DOCUMENTS

| EP | 0672179 | 3/1993 |
| EP | WO 93/05179 | 3/1993 |
| EP | 0575845 | 12/1993 |
| EP | WO 95/01453 | 1/1995 |
| EP | WO 95/07345 | 3/1995 |

OTHER PUBLICATIONS

Clay et al. The Lancet. May 1991. vol. 337(8749) 1049–1052.*
Computer–aided wheat cultivar identification and analysis of densitometric scanning profiles of fliadin electrophoregrams—H.D. Sapirstein and W. Bushuk.*
Biomagnetic Techniques in Molecular Biology. Dynal. Section 10.1, p. 116. 1995.*
Biomagnetic Techniques in Molecular Biology, Dynal, Section 10.1, p. 116, 1995.
Eiermann, T. H., et al., "HLA–DPB1 Oligonucleotide Typing of a Southwest German Caucasian population," Tissue Antigens, 38, pp. 193–198 (1991); Munksgaard International Publishers, Ltd.
Gao, X., et al., "Characterization of the HLA–A Polymorphism by Locus–Specific Polymerase Chain Reaction Amplification and Oligonucleotide Hybridization," Human Immunology, vol. 41, pp. 267–279 (1994); Elsevier Science Publishing Co., Inc.
Zimmerman, P. et al., "Optimizing Probe Selection in Directed Heteroduplex Analysis Using HDProbe 1.1," BioTechniques, vol. 19, pp. 972–977 (Dec. 1995); Eaton Publishing Co.
Zimmerman, P., "Exploiting structural differences among heteroduplex molecules to simplify genotyping the DQA1 and DQB1 alleles in human lymphocyte typing," Nucleic Acids Research, vol. 21, No. 19, pp. 4551–4547 91993); Oxford University Press.
Zimmerman, P., et al., "Migration of a Novel DQA1* Allele (DQA1*0502) from African Orgin to North and South America," Human Immunology, vol. 42, pp. 233–240 (1995); Elsevier Science Publishing Co., Inc.

* cited by examiner

*Primary Examiner*—Juliet C. Switzer
(74) *Attorney, Agent, or Firm*—Medlen & Carroll, LLP.

(57) ABSTRACT

The invention provides a method for separating a DNA molecule from a mixture of DNA molecules, which method comprises: (i) amplifying the DNA molecules in the mixture; (ii) hybridising single strands of the amplified DNA molecules with a complementary strand of a reference DNA molecule so as to form duplexes; and (iii) separating the duplexes. The different DNA molecules in the original mixture give rise to duplexes having different numbers, positions or types of mismatches. This allows the duplexes to be separated by, for example, gel electrophoresis. The separated duplexes can then be analysed to identify the DNA molecules that were present in the original mixture.

19 Claims, 14 Drawing Sheets

1 2 3 4 5 6 7 8 9 10

1 2 3 4 5 6 7 8 9 10

M | A B Cw | A B Cw | A B Cw
      HS67        M7         AM

Fig.8.
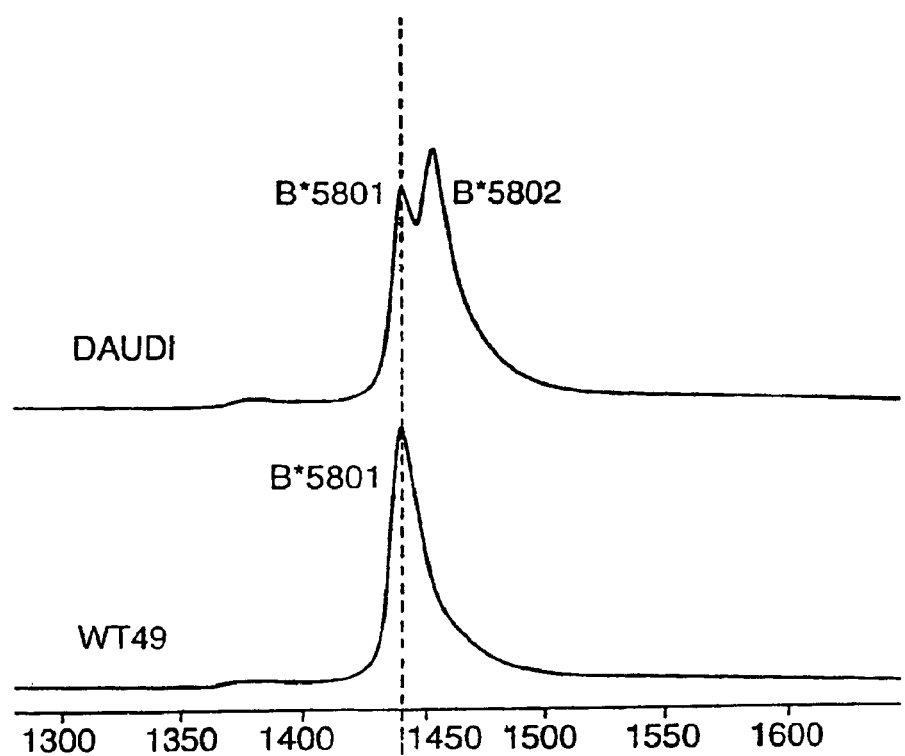
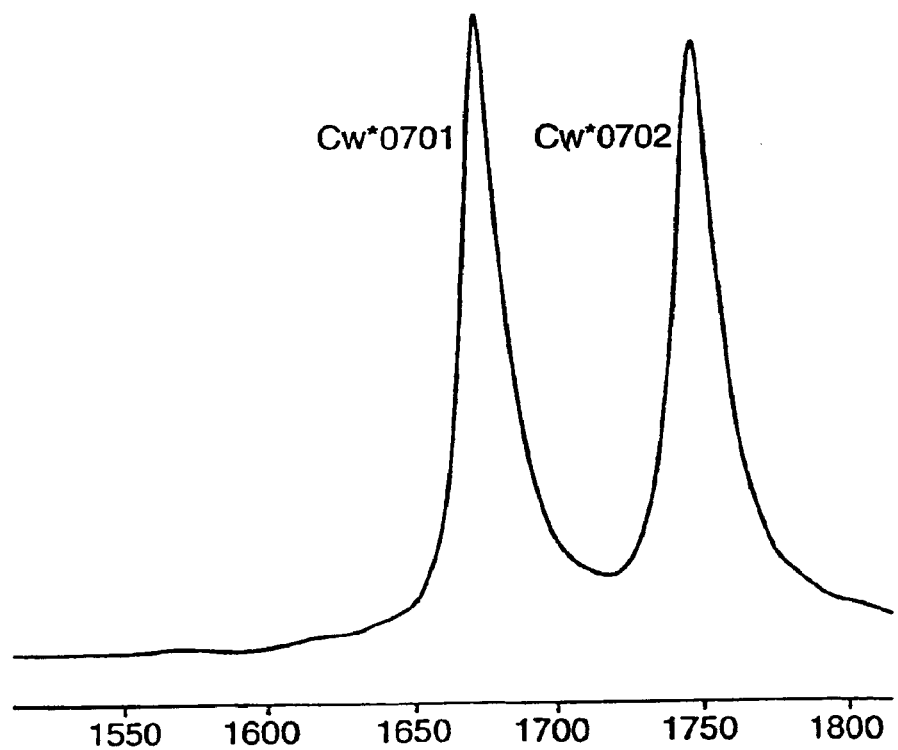

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
gaaacsgcct ctgygggag aagcaa                                    26

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
ctccctctgt taaccctggt tgt                                      23

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gggaggagcg agggaccsc ag                                        22

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tatccagcgg ccctaccgg agg                                       23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
agcgaggkgc ccgcccggcg a                                        21

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6 tcaccctcg gaagggtag agg                                        23

METHODS FOR SEPARATING AND/OR IDENTIFYING DNA MOLECULES

The invention relates to methods for separating and identifying DNA molecules in mixtures of DNA molecules having the same number of nucleotides but different base sequences.

1. BACKGROUND TO THE INVENTION

1.1 General Introduction

Many genes exist as multiple alleles which differ from each other by small differences in sequence. Individuals are often heterozygous with respect to the alleles of particular genes; i.e. individuals often have two different alleles of the same gene.

In some circumstances, it is desirable to separate the alleles of a gene from a mixture of the alleles. For example, when it is desired to carry out a test to determine which alleles of a gene are carried by a heterozygous individual, it is often necessary to separate the two alleles before carrying out the test because the presence of two alleles in one test can prevent meaningful results from being obtained.

In view of the fact that the difference between the alleles of a gene can be as little as one nucleotide, it is often difficult to separate the alleles from a mixture of the alleles. These difficulties are increased in genes which have a large number of different alleles, such as the major histocompatibility complex (MHC) genes (e.g. the human leucocyte antigen (HLA) class I and II genes which have over 500 known alleles).

Identity of alleles is frequently essential in a clinical setting, for example, HLA matching between a bone marrow or kidney recipient and donor is one of the major factors influencing transplant success. Up to date the most favourable bone marrow transplant (BMT) and kidney transplant results have been obtained using sibling donors who are genotypically HLA-identical to the recipient but such donors are available for only about 30% of patients[1-5]. BMT using unrelated donors can be successful, but these transplants have higher rates of graft failure, increased incidence and severity of Graft versus Host Disease and more frequent complications related to delayed or inadequate immune reconstitution [4].

New molecular biological methods for detection of genetic polymorphism currently provide an opportunity to improve e.g. HLA matching of unrelated donors as well as a research tool to investigate the relationship between disparity and transplant complications. These molecular typing methods include sequence-specific amplification, hybridisation with oligonucleotide probes, heteroduplex analysis, single strand conformation polymorphism and direct nucleotide sequencing.

Each of these molecular approaches has been used for routine HLA class II typing [6], but a variety of reasons related to the HLA class I gene structure has complicated their application to class I typing. The reasons for these limitations are the extensive polymorphism of each class I locus and the degree of sequence homology between the loci. In addition, sequence homology between class I classical and non-classical genes and the reported 12 pseudo genes can cause problems for specific locus amplification[7].

The low extent of "allele specific" sequences at polymorphic sites is a feature of the HLA class I genes that has limited the resolution of all current DNA typing approaches. An "allele specific" sequence is a sequence that is only present in one allele and can therefore be used to distinguish the allele from other alleles.

The main problem which complicates the identification of an allele is the presence of a mixture of alleles, as well as contamination by segments of DNA which have homology to the allele it is wished to identify and which are co-amplified in PCR. Current typing methods are sometimes unable to resolve the allele it is wished to identify from contaminating DNA fragments. Separation techniques such as single strand conformation polymorphism (SSCP) can only partially resolve this problem.

Methods for Allele Separation

1.2 Sequence Specific Primer Amplification (PCR-SSP)

This method utilises both the group-specific and, when present, allele-specific sequence sites in PCR primer design. The SSP design is based on the amplification refractory mutation system (ARMS), in which a mismatch at the 3' residue of the primer inhibits non-specific amplification[8,9].

Although each SSP reaction may not individually provide sufficient specifity to define an allele, the use of combinations of sequence specific primers allows the amplification of their common sequences to give the desired HLA specificity.

However, despite its high accuracy, PCR-SSP is only in some cases more informative than serology. The reason for this is the low occurrence of allele specific sequence motifs in the exons and this limitation has stimulated a vast amount of research into the identification of allele specific motifs even in the intron sequences[10]. However, up to date this approach has not contributed considerably to the identification of more alleles.

Another limitation of this method is that it detects a limited number of polymorphic sequences which are utilised to predict the entire sequence. If an unknown allele is present in a particular sample this extrapolation may be incorrect.

In addition, the successful use of the technique relies on group specific amplification and therefore prior knowledge of broad HLA specificity is needed.

1.3 Single Strand Conformation Polymorphism (SSCP)

This technique is based on the electrophoretic mobility of single stranded nucleic acids in a non-denaturing polyacrylamide gel, which depends mainly on sequence-related conformation[11-13]. The technique can be employed for isolating single alleles which could then be used for further manipulation and analysis such as direct sequencing. The pattern of bands obtained after electrophoresis may be diagnostic for an allele[14,15].

The major disadvantage of SSCP is the tendency of DNA single strand to adopt many conformational forms under the same electrophoretic conditions resulting in the presence of several bands from the product; this makes the identification more difficult. In addition there is a high degree of variation and inconsistency in the sensitivity of this method for detecting mutations or allelic variations and there is a physical limitation in the size of the DNA fragment which is of the order of 200–400 base pairs[16].

1.4 Denaturing Gradient Gel Electrophoresis (DGGE) and Temperature Gradient Gel Electrophoresis (TGGE) [17,18]

The underlying principle of both techniques is the difference in the degress of melting between two alleles (double stranded DNA) which results in a reduction of mobility of the DNA fragments in polyacrylamide gels containing a denaturing reagent (DGGE) or a temperature gradient (TGGE).

Both techniques have been used frequently for screening mutations in genetic systems with one or two variants. They are only rarely used for the separation of alleles in highly polymorphic systems such as HLA.

Both techniques require specific conditions for a particular system under investigation and, in addition, where two alleles share common sequence segments with low melting points they may not always be differentiated. The simultaneous melting of both alleles will produce very similar retardations.

1.5 Cloning of DNA

This is the classical method of preparation of a single sequence, i.e. the sequence derived from a single allele. A variety of constructs has been used to introduce the required DNA fragment into a plasmid and grow sufficient copies for analysis. This method yields pure samples of the analyte, but is time consuming to perform and several clones are normally tested to ascertain the homogeneity of the product.

Methods for the Identification of Alleles 1.6 Heteroduplex Analysis

Fully matched DNA duplexes are more stable than those with base mismatches. Instability of the duplex increases with the number of nucleotide mismatches; these cause formation of loops and bends in the linear DNA fragment which produce an increasing "drag effect" in polyacrylamide gels which retard the affected migrating bands[19-21].

Mismatched DNA hybrids (heteroduplex) may be formed at the end of each PCR cycle between coamplified alleles from a particular locus or loci due to primer cross reaction at sites with similar sequences. During the annealing stage of each cycle of the PCR, a proportion of sense strands of each allele may anneal to anti-sense strands of different alleles. The banding pattern obtained in PAGE analysis can be useful for identifying the alleles involved in the reaction[22-24].

Heteroduplex analysis is an approach that has been utilised to compare HLA genes of a particular donor and recipient. HLA genes are amplified, denatured (melted into single strands) and mixed together under conditions that promote renaturation to form double stranded molecules. If the HLA genes of a donor and recipient are similar but not identical, heteroduplexes will form consisting of one strand of an allele of donor origin and a second strand from a different allele of recipient origin[25,26]. The sensitivity of this method can be increased by adding DNA from an HLA allele that is not present in the donor or recipient.

The major advantage of heteroduplex analysis is that it is relatively easy and inexpensive. Limitations of this approach include inability to detect certain HLA disparities, potential detection of irrelevant silent mutations and lack of specific information regarding the nature of the alleles involved.

Up to date this approach has been used for HLA class II typing with limited success. Its application to class I typing has not been successful.

1.7 Sequence Specific Oligonucleotide Probes (PCR-SSO)

SSO typing involves amplification of HLA alleles from a particular locus followed by hybridisation with a panel of oligonucleotide probes to detect polymorphic sequences that distinguish one allele or group of alleles from all others. In polymorphic systems a one step operation may not always differentiate all the known alleles; selected primers can be used to achieve amplification of individual alleles which are then identified by specific probes. This second stage of oligotyping is often referred to as high resolution oligotyping[6].

The advantages of the PCR-SSO method are specificity, sensititivity, simplicity, reproducibility, and it is relatively inexpensive to operate and allows simultaneous processing of many samples. This approach has been applied successfully, for example, to typing of HLA class II alleles.

The major methodological drawback of this approach is that the complexity of the technique is directly related to the number of alleles under investigation and the presence of two alleles in the heterozygous condition can complicate the identification process.

Publishing oligotyping methods could result in incorrect interpretation of data if certain combinations of recently discovered alleles are present in a specimen. It is therefore necessary to update the reagents used in the identification step. Several typing approaches for HLA-A and B based on PCR-SSO have been published; these typically require over 40 and 90 probes respectively[27,28]. The operation of these methods is time consuming and the resolution obtained is only moderate.

1.8 Nucleotide Sequencing

DNA templates for sequencing can be produced by a variety of methods, the most popular being the sequencing of cloned genomic or cDNA fragments, or the direct sequencing of DNA fragments produced solely by PCR (as in 1.2 above). These templates represent a single sequence derived from one haplotype. Alleles from both haplotypes of a heterozygous sample may be co-amplified and sequenced together using locus-specific PCR primer.

The recent availability of computer software, which allows the user to align the derived sequence against established sequence libraries, has facilitated the analysis and allele assignments for heterozygous samples in which both a templates are sequenced at the same time[27]. The effectiveness of this method depends on the amount and frequency of ambiguous heterozygous combinations, for example there are many HLA class II alleles that when present together in one sample cannot be differentiated by this method. The number of such ambiguous combinations of allele sequences is even greater for HLA class I alleles.

Up to date two HLA class I typing approaches based on direct sequencing have been published. Both require serology information followed by allele specific PCR amplification and then direct sequencing[14,30]. More recent practice, however, is to amplify DNA fragments without prior knowledge of the allele groups and to use locus specific PCR amplification. Theoretically these approaches should give the highest resolution, but they are beset by ambiguous sequence combinations which cannot be resolved satisfactorily and in practice these methods are expensive and difficult to perform routinely.

2. SUMMARY OF THE INVENTION

The invention provides methods for separating and/or identifying a DNA molecule in a mixture of DNA molecules. The separation methods comprise (i) amplifying the DNA molecules in the mixture;

(ii) hybridising single strands of the amplified DNA molecules with a complementary strand of a reference DNA molecule so as to form duplexes; and (iii) separating the duplexes.

It is possible to isolate the single strands of the amplified DNA molecules between steps (i) and (ii), and hybridise these isolated single strands with an isolated complementary strand of a reference DNA molecule in step (ii).

Alternatively, the duplexes of amplified DNA formed in step (i) can be used in unisolated form in step (ii). In this case, the amplified duplexes may be contacted directly with a reference DNA molecule containing a labelled strand in step (ii). Only the single strands of the amplified duplexes which hybridise to the labelled strand of the reference DNA molecule are detected in any subsequent detection step.

The different DNA molecules in the original mixture give rise to duplexes having different numbers, positions and/or types of mismatches. This allows the duplexes to be separated by, for example, gel electrophoresis. The separated duplexes can then be analysed to identify the DNA molecules that were present in the original mixture. Two embodiments of the method of the invention are illustrated in FIGS. 1 and 2.

The method of the invention can be used directly as a diagnostic technique to identify a DNA molecule by the use of a specific reference DNA molecule. The formation of a homoduplex identifies a DNA molecule in the unknown mixture as identical to the reference DNA molecule. The formation of a heteroduplex may also be used to identify an unknown DNA molecule by using a known heteroduplex as a control. The invention includes a method for identifying a DNA molecule, which method comprises (i) contacting the DNA molecule with a labelled reference DNA strand under conditions such that the reference stand hybridizes to a complementary strand of the DNA molecule so as to form a test duplex; (ii) running the test duplex and one or more control duplex(es) in a gel by electrophoresis; and (iii) comparing the position of the test duplex on the gel with the position(s) of the control duplex(es).

The method of the invention can also be used as a separation technique for separating the alleles in a mixture of unknown alleles of a polyallelic gene, such as the mammalian MHC genes (e.g. the HLA genes). Duplexes formed between the unknown alleles and a reference allele are separated so as to isolate the unknown alleles for identification by techniques such as DNA sequencing, SSP and SSO.

The use of a single reference DNA molecule is effective for separating and/or identifying many DNA molecules, such as alleles from genetic loci in which there is only a small number of different alleles existing in the population. However, we have found that the use of two reference DNA molecules is unexpectedly advantageous, especially where there is a great number (e.g. from 10 to 300 or from 30 to 100) of alleles in the population, such as in the case of the HLA genes. For some genes, there may be two or more different alleles that give duplexes that migrate to the same position with a single reference strand. We have now found that such alleles may be distinguished from each other by using a second reference strand that forms duplexes that migrate to different positions. The combined results for two reference strands give a unique parameter for each allele. In some circumstances a third reference strand may be desirable, but two reference strands will resolve most ambiguities of allelic type, even at genetic loci such as HLA in which there is a great variety of allelic type.

The effectiveness of using two reference strands is illustrated by, for example, FIGS. 7 and 9. These Figures show that the two HLA class I alleles A*3001 and A*0201 migrate to similar positions when A*0101 is used as the reference strand, and it would therefore be difficult to distinguish between these two alleles using the A*0101 reference strand alone. However, when A*0217 is used as the reference strand, the two alleles are separated by a great distance. Thus, the combination of reference strands A*0101 and A*0217 allows unambiguous identification of the alleles, whereas the use of only one reference strand would not. Since the HLA loci are among the most complex known, it is clear that the invention is broadly applicable to a wide variety of genetic loci, even those that are complex in their genetic variation.

In one embodiment, the invention provides a method which comprises (i) amplifying the DNA molecules in the mixture employing a pair of primers in which one of the primers carries a ligand, so as to produce an amplified mixture of double-stranded DNA molecules in which one of the strands carries a ligand;

(ii) contacting the amplified mixture of double-stranded DNA molecules with a receptor on a solid support under conditions such that the ligand binds to the receptor;

(iii) separating the mixture of double-stranded DNA molecules into single-strands and removing the strands that are not bound to the support by the ligand;

(iv) recovering the remaining strands from the support;

(v) mixing the recovered strands with a complementary strand of a reference DNA molecule so as to form duplexes; and (vi) separating the duplexes.

This embodiment and all subsequent applications of the embodiment may be modified by recovering the single-strands that do not bind to the support in step (iv), and using these strands instead of the strands which bind to the support to form duplexes in step (v).

The complementary strand of the reference DNA molecule may be provided by essentially the same technique as the technique set out above in steps (i) to (iv) for providing the mixture of DNA molecules in single-stranded form. In particular, the reference complementary strand DNA molecule may be provided by (i) amplifying the reference DNA molecule employing a pair of primers in which one of the primers carries a ligand, so as to produce amplified double-stranded reference DNA molecule in which one of the strands carries a ligand;

(ii) contacting the double-stranded reference DNA molecule with a receptor on a solid support under conditions such that the ligand binds to the receptor;

(iii) separating the double-stranded reference DNA molecule into single-strands and removing the strand that is not bound to the support by the ligand; and (iv) recovering the remaining strand from the support.

In another embodiment of the invention, there is provided a method which comprises (i) amplifying the DNA molecules in the mixture employing a pair of primers in which one of the primers carries a high molecular weight molecule, so as to produce an amplified mixture of double-stranded DNA molecules in which one of the strands carries a high molecular weight molecule;

(ii) separating the mixture of double-stranded DNA molecules into single strands;

(iii) mixing the single strands with a complementary strand of a reference DNA molecule so as to form duplexes; and (iv) separating the duplexes.

The complementary strand of the reference DNA molecule may be provided by (i) amplifying the reference DNA molecule employing a pair of primers in which one of the primers carries a high molecular weight molecule, so as to produce an amplified double-stranded reference DNA molecule in which one of the strands carries a high molecular weight molecule; and (ii) separating the double-stranded reference DNA molecule into single strands.

This embodiment overcomes the need for solid support systems by conjugating one primer of a pair of primers directly to a high molecular weight molecule (e.g. a protein), for the reference and test systems. The amplified product after hybridisation can be applied directly to a separating gel. The high molecular weight conjugates are retained in the gel compared to the duplex without attachment of the high molecular weight molecule.

In a further embodiment of the invention, there is provided a method which comprises (i) amplifying a single strand of each of the DNA molecules in the mixture;

(ii) mixing the amplified single strands with a complementary strand of a reference DNA molecule so as to form duplexes; and (iii) separating the duplexes.

In this embodiment, the complementary strand of the reference DNA molecule may be provided by amplifying a single strand of the reference DNA molecule. The amplification of the single strand of the reference or test DNA molecule can be done, for example, by asymmetric PCR.

This embodiment overcomes the need for both solid support systems and conjugation of one primer of a pair to a high molecular weight molecule. However, in the embodiment it is possible to use a primer carrying a ligand such as a hapten in order to facilitate capture of the amplified strand with a receptor such as an antibody and separation of the amplified strand from other components in the amplification mixture.

After separation of the DNA molecules by one of the above methods, the molecules present in the mixture may be identified by carrying out one or more of the following steps:

(i) comparing the positions of the separated duplexes on the gel with the position of a control DNA;

(ii) sequencing each of the separated molecules;

(iii) sequence specific primer (SSP) amplification analysis; and (iv) sequence specific oligonucleotide (SSO) analysis.

The invention provides an improvement over prior methods for separating DNA molecules. The advantages offered by the invention can be summarised as follows:

(a) The invention provides a high resolution between different DNA molecules and differences of as little as one nucleotide between molecules can be detected.

(b) The invention allows simultaneous and rapid processing of a large number of samples.

(c) The invention is comparatively inexpensive to perform, particularly when compared to prior methods which achieve a high level of resolution.

(d) The invention uses techniques that can be performed easily without recourse to complex and expensive technology.

3. PRINCIPLE UNDERLYING THE INVENTION

Fully matched DNA duplexes are more stable than those with base mismatches. Regions of nucleotide sequence which are complementary retain the double stranded structure, but mismatched regions form single-stranded loops which induce kinks along the length of the DNA molecule. Relative to a reference strand, the number, size, composition and position of the single-stranded loops vary for each allele. Heteroduplex DNA migrates more slowly than the corresponding homoduplex DNA. Both denaturing reagents and/or heat enhance the effect of the mismatches. Since the rate at which the DNA migrates in polyacrylamide or special agarose gels depends on both molecular conformation and molecular weight, the described method of introducing conformational changes in the hybrid duplex provides the basis of highly specific separation of alleles.

As the molecular conformation of heteroduplexes can be manipulated by hybridisation of a known single strand reference with unknown complementary single strand(s), it is proposed that heteroduplexes can be separated from each other by e.g. denaturing or non-denaturing polyacrylamide electrophoretic analysis. This allows the separation of the two amplified alleles from a particular locus for further analysis. In addition, the method of the invention (which we call "Complementary Strands Analysis" (CSA)), permits assessment of the quality of the PCR product before the process of identification is carried out. CSA is able to identify the presence of coamplified non-desirable alleles from different loci and, potentially, PCR fragments that contain artifacts such as Taq errors and in vitro recombinations.

In addition, CSA itself can be used as a diagnostic technique. It can identify alleles by hybridisation of allele specific single strand with unknown complementary single strand(s) followed by e.g polyacrylamide gel electrophoretic analysis, with or without denaturing conditions and/or with or without a temperature gradient. The formation of a homoduplex demonstrates identity between at least one of the unknown alleles and the allele specific reference, and non-identity between them produces heteroduplex(es).

4. DETAILED DESCRIPTION OF THE INVENTION

The kinds of DNA molecule that may be separated and identified by the methods of the invention include alleles of polyallelic genes, segments of genes and non-expressed fragments.

Examples of genes with multiple alleles to which the invention may be applied are the mammalian MHC genes such as the HLA class I and class II genes, the T cell receptor genes in mammals [33,34], TAP, LMP, ras[32], non classical HLA class I genes, the genes for human complement factors C4 and C2, Bf in the human HLA complex, and genes located in mitochondrial DNA, bacterial chromosomes and viral DNA. The invention can be used in the analysis and identification of mutations (e.g. point mutations) in these and other genes and chromosomal aberrations such as translocation, deletions and inversions.

There are three different genes within the HLA class I group of genes, namely HLA-A, HLA-B and HLA-C, and each of these three genes exists in the form of multiple alleles. There are a total of about 222 known alleles of the HLA-A, HLA-B and HLA-C genes and the sequences of known alleles are set out in Arnett and Parham (1995) Tissue Antigens 45 217–257. There are also multiple genes within the HLA class II group of genes, known as DR, DQ and DP.

In the method of the invention, it is necessary to identify primer sequences unique for the target gene so as to include all polymorphic sites of interest in the amplified fragment, which should also be manageable in length. For example, the polymorphic sites in exons 2 and 3 of HLA class I would facilitate the identification of all recognised alleles of HLA-A, B and C, with 5 exceptions. Therefore, the primers used in the invention may, for example, be selected so as to specifically amplify exons 2 and 3 of each of HLA-A, HLA-B and HLA-C separately. Cereb[31] and collaborators have described primer sequences located in the first and third exons which can be used for locus-specific amplification of the entire exon 2 and 3 region of each of the HLA-A, HLA-B and HLA-C genes. The sequences of suitable primers are given in Example 1 below.

The reference DNA molecule used in the invention may have a known sequence. The reference may be chosen so as to have a similar allotype to an allotype that at least one of the test alleles is suspected of having. For example, it may be known that a test allele is of the HLA-A02 type from serological data, but it may not be known which of the seventeen A02 sub-types the allele is. In this case, the reference allele may be chosen to be of sub-type A0201 and the method of the present invention could then be used to determine which of the A02 sub-types the test allele is.

The reference strand may be obtained from (a) a homozygous source, (b) a heterozygous source from which individual strands are isolated by gel separation after amplification steps or (c) DNA synthesis. There are now about 500 internationally recognised cell lines which contain HLA alleles of known sub-type and these cell lines can be used as a source of reference alleles.

The control DNA used in the method of the invention may be a homoduplex between two strands of the same DNA molecule (e.g. the reference DNA molecule), so that migration of a test duplex to the same position on the electrophoretic gel as the control homoduplex indicates that the test duplex is a homoduplex. If the test duplex is a homoduplex, it can be concluded that the unknown DNA molecule is the same as the reference molecule.

Control DNAs may be obtained by simply amplifying a known DNA molecule using the same primers as used in the method of the invention to amplify the reference and unknown molecules.

The control DNA may also be a heteroduplex of known DNA molecules. This allows the method of the invention to be used to identify molecules in heteroduplexes formed by test samples. The same heteroduplexes from different sources migrate to the same position on a gel.

A potential problem with identifying molecules in heteroduplexes is that certain different heteroduplexes may contain combinations of mismatches which cause them to migrate to the same position. A method for overcoming this problem would be to use a second reference strand which provides different combinations of mismatches.

In typing of the HLA class I alleles, the different duplexes could be identified by their different sizes (the HLA-A, HLA-B and HLA-C genes are different sizes) or by amplifying each of the HLA-A, HLA-B and HLA-C genes with primers carrying different labels. Each locus specific heteroduplex would have a different size or carry a different label, and could be electrophoresed simultaneously in the same track of a gel. The duplexes could then be identified by comparing them to control duplexes in the same gel. Examples of suitable labels include radiolabels, colour labels and fluorescent labels.

The mixture of alleles used in the method of the invention may be from a prospective donor or a prospective recipient in a tissue or organ transplant operation. The results of the method may therefore be used to match a prospective recipient with a prospective donor.

In one embodiment of the invention, the alleles of the prospective donor or of the prospective recipient are in effect used as reference alleles and duplexes are formed between strands of the prospective recipient's alleles and of the prospective donor's alleles. Analysis of the duplexes formed between the strands from the prospective recipient and donor reveals whether they have the same alleles. Thus, in one embodiment, the invention provides a method for determining whether a prospective recipient in a tissue or organ transplant operation has alleles of a gene that are compatible with the alleles of a prospective donor in the operation, which method comprises (i) amplifying the alleles of the prospective recipient employing a pair of primers in which one of the primers carries a ligand, so as to produce amplified double-stranded alleles of the prospective recipient in which one of the strands carries a ligand;

(ii) contacting the amplified double-stranded alleles with a receptor on a solid support under conditions such that the ligand binds to the receptor;

(iii) separating the double-stranded alleles into single-strands and removing the strands that are not bound to the support by the ligand;

(iv) recovering the remaining strands from the support;

(v) mixing the recovered strands with complementary strands of the alleles of the prospective donor so as to form test duplexes;

(vi) separating the test duplexes by gel electrophoresis; and carrying out one or more of the following steps:

(vii) comparing the positions to which the test duplexes migrate on the gel with the position of a control DNA;

(viii) sequencing one or both strands of each of the test duplexes;

(ix) sequence specific primer (SSP) amplification analysis; and (x) sequence specific oligonucleotide (SSO) analysis.

Other proposed uses of the invention include determination of the paternity of an individual by identifying one (or more) of his alleles to see if it is the same as a corresponding allele of a putative father. The invention may also be used in forensic medicine to determine the origin of a sample of body tissue or fluid, as a follow up technique in treatment of haematological malignancies or inherited disorders, in adoptive immunotherapy, and in identification of bacteria and viruses.

In the method of the invention, the amplification steps may be carried out by polymerase chain reaction (PCR).

The ligand/receptor system used in the invention may, for example, be the biotin/streptavidin system or a hapten/antibody system. Direct conjugation of the primer via a linking group, such as short poly A, to the beads is an alternative. When the biotin/streptavidin system is used, one of the primers used in each of the amplification steps may be labelled with biotin, so that when the amplification reaction is carried out double-stranded DNA is produced in which one strand carries a biotin label. The double-stranded DNA may then be bound to a solid support coated with streptavidin.

The solid support used in the invention is typically magnetic beads. However, other supports may be used, such as the matrix of an affinity chromatography column. When the support is in the form of magnetic beads, the two strands of the amplified DNA are separated by attracting the beads to a magnet and washing the beads under conditions such that the double-stranded DNA dissociates into single-strands. The dissociation is typically performed by incubating the beads (e.g three times) under alkaline conditions (e.g. 0.1 M or 0.15 M NaOH) at room temperature for about 5 or 10 minutes. Usually, the strand which is not bound to the support by the ligand is then discarded, although it is equally possible to retain the strand that is not bound to the support and discard the strand that is bound to the support.

The strand that remains attached to the support may be recovered from the support by incubating the support under conditions such that the ligand/receptor complex dissociates.

When the biotin/streptavidin system is used, the support is typically heated to e.g. 95° C. for about 5 minutes; this ensures denaturation of the streptavidin molecule to release the biotinylated single strand which is then recovered.

At this stage, there have been provided a single-stranded unknown allele and the complementary strand of a reference allele. The two strands are then mixed together under conditions in which they hybridise to form duplexes. Typically, the hybridisation step is performed by heating the mixture of strands fat about 95° C. for about 3 min, at about 70° C. for about 5 min and then at about 65° C. for about 45 min.

Under these conditions, duplexes are formed which can subsequently be separated by gel electrophoresis (e.g. polyacrylamide gel electrophoresis). The electrophoresis may be carried out under denaturing conditions because this may enhance separation.

As an alternative separation technique to gel electrophoresis, high pressure liquid chromatography (HPLC) may be used.

In the embodiment of the invention in which one of the pair or primers is conjugated to a high molecular weight molecule, the molecule may be a protein such as bovine serum albumin (BSA). The molecular weight of the high molecular weight molecule is such that it causes the DNA molecule to which it is attached to be sufficiently retarded in the separation step (e.g. the electrophoresis step) to allow the DNA molecule to be separated from a duplex without a high molecular weight compound attached. For example, the molecular weight of the high molecular weight molecule may be from 10 to 200 kDa, preferably 20 to 100 kDa.

In a preferred embodiment of the invention, DNA fragments from a particular segment of a genome can be separated and identified with the use of a labelled reference strand without the isolation of the duplex from the separation phase. This approach can be automated with the use of currently available technology for simultaneous resolution and identification of alleles.

In this diagnostic use of the method, separation of the sample DNA fragments into a single strand or the use of ligand bearing primers is not necessary. The pre-labelled reference strand is mixed with the sample and, following the hybridisation step, the mixture is analysed by a method which will separate the DNA duplexes (eg electrophoresis or high pressure liquid chromatography). This embodiment is referred to as "Double Strand Conformation Analysis" (DSCA).

The selective identification of the marker bearing reference-sample duplexes excludes those hybrids which have not complexed with the reference strand. The position of the identified bands is diagnostic. These can be accurately assigned by the inclusion of reference mobility markers, which could be (a) internal markers with faster and slower mobilities than the duplex under investigation or (b) multiple markers that, for electrophoretic runs, would be resolved simultaneously in a separate track and would form a reference ladder of graded mobilities.

In this embodiment, the DNA sample fragments can be obtained by (a) specific amplification, e.g. PCR, or (b) enzymatic digestion of the genome where the number of genes is limited (e.g. viral genomes, microbial plasmids, vector cassettes or the segments from (a)).

The reference strand, which is partially complementary in sequence to the intended sample target, may be prepared by introducing specific nucleotides at selected positions which enhance the separation of the duplexes during the separation stage. The reference strand may be synthetic, i.e. man made and not from any naturally-occurring allele. An optimum reference can be designed which produces an optimised distribution of bands. A second and further references can be used which improve the resolution of the bands which are not well resolved by the use of a single reference. This improves the accuracy of the identification, in particular for closely related alleles.

The reference may be synthesised:

a. By a combination of specific primers which generate a strand with three nucleotide differences at 3' end; this would ensure the specificity of the amplification following the separation of the sample strands.

b. By preparing short fragments of target sequence either by specific amplification or where necessary synthetically. After specific alterations to the sequences these fragments would be ligated to produce a single reference strand.

c. The reference strand may have a fluorescent ligand attached at one end for identification or it could carry a ligand or compound (e.g. biotin) that would allow attachment of an enzyme molecule (e.g. via streptavidin). The reference-sample duplex can then be identified either by fluorescence detection methods or by enzyme amplified methods using e.g. a colourometric or chemiluminescent technique.

This approach is suitable for automated seperation and detection. In order to automate the analysis, it is proposed to include mobility markers in the seperation phase. These labled markers would be either defined segments of genomic DNA prepared by amplification or synthetically prepared so as to act as reference points for automatic computation of the exact position of the sample under investigation.

Use of the invention to analyse ras oncogene point mutations:—ras has been implicated in the oncogenesis of many tumours and appears to be activated by point mutations. These mutations can occur in all three ras genes (N-ras, Harvey-ras and Kirsten-ras) at codons 12/13 and 61 with corresponding amino acid substitutions in ras proteins (p21). These point mutations can be detected by application of the invention.

Two pairs of primers are needed, one for the 12/13 codons and one for codon 61. The primers described by Lyons [22] can be used, with modification by covalent attachment of a ligand to one primer of each pair for each of the test fragment and the reference fragment. For example, a ligand may be attached to primer Pla (a 12/13 codon primer) and primer P1b (a 61 codon primer) for the reference fragment, and to primer P2a (a 12/13 codon primer) and primer P2b (a 61 codon primer) for the test fragment. In this way, complementary ligand-labelled single strands for the reference and test fragments are obtained. The complementary strands are hybridised and subjected to electrophoresis. Detection of a homoduplex between the test fragment and a mutant reference fragment will indicate the presence of the mutation in the test fragment.

Use of the invention to identify T cell receptor (TCR) rearrangements in T cell tumours and in adoptive immunotherapy:—some T cell tumours can be monoclonal in origin and a proportion of the T cells from a patient may carry a particular rearrangement of the T cell variable domain genes alpha/beta or gamma/delta depending on the T cell type. The efficacy of a particular treatment or the course of the disease can be evaluated by the identification of the malignant clone TCR rearrangement. The method of the invention with the use of suitable number of controls can be made semi-quantative, which would allow the evaluation of the progress of the treatment or the disease.

In adoptive immunotherapy, a specific rearrangement of the variable domain genes of the TCR can be used as a marker for the selected cytotoxic T cell that has been generated in-vitro. Post infusion fate of these cells can be monitored by a semi-quantative detection of the particular rearrangement.

In both methods the T cell variable domain gene primers [33,34] can be modified by covalent attachment of a ligand at the 5' end of the primer pair, and the reference strand will be selected to be complementary to the test DNA fragments.

The following Examples illustrate the invention.

Following HLA A locus specific amplification of exons 2 & 3, the antisense DNA strands were isolated as described in Example 1 below and hybridised with complementary locus reference strand. Samples were applied to PAG/agarose cassette and electrophoresis was performed at 230 volts for 6 hrs at room temperature; the gel was stained with SYBR Green I. Single bands were obtained from homozygous cell lines and double bands from heterozygous lines. Duplexes from identical alleles have the same mobility in the gel. Samples in lanes 5 and 8 are from alleles A0101 and A0201, and samples in lanes 1 and 9 are from homozygous line with A0101 which has the same mobility as the fast lines in lanes 5 and 8.

Figure 4:
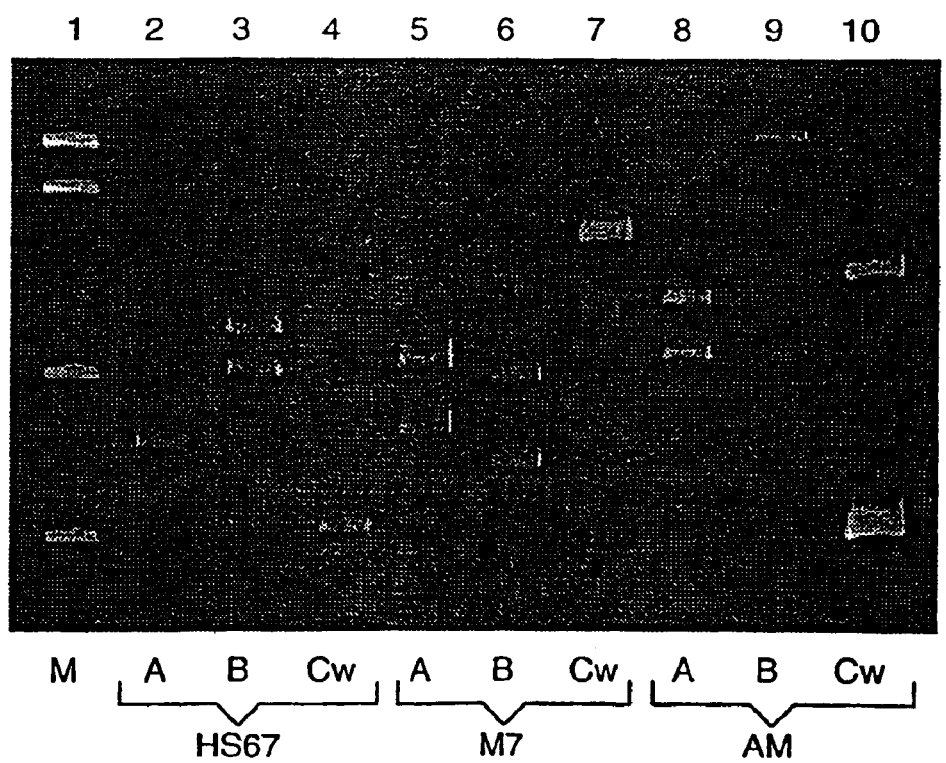

FIG. 4 shows analysis of HLA class I locus DNA fragments from three cell lines separated by CSA in non-denaturing PAGE with the use of reference strands from each locus.

PCR products of locus specific amplification were processed to isolate anti-sense single strands, and these were hybridised with complementary reference strands (A*0101, B*4402 and Cw*0701) as appropriate.

M=marker DNA fragments; HS67 alleles, A=1101 and 2402, B=5801 and 6701, Cw=0701/unknown; M7 alleles, A=0202 and 0301, B=5301 and 35(serology), Cw=4 (serology) homozygous; AM alleles, A=0205 and 3201, B=4901 and 5301? (Standard for identification not available), Cw=0701 and 10(serology). For serological types allelic standards were not available for identification. The homozygous Cw sample M7 yields a single band (lane 7).

Figure 5:
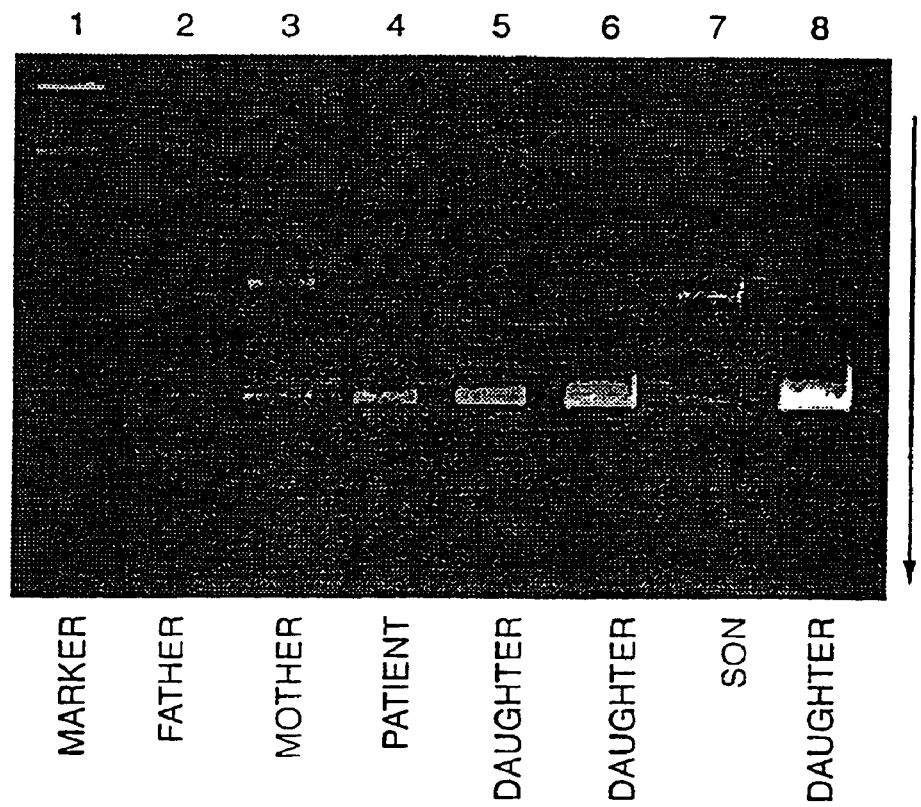

FIG. 5 shows the results of an experiment in which CSA was used to cross-match HLA-B alleles in an attempt to identify a potential bone marrow donor from a family of seven.

Parents and siblings were typed by serology only and CSA was used to identify a match. DNA was amplified with locus specific primers and the PCR products were processed to isolate anti-sense single strands. These were hybridised with complementary reference strand B*4402. The duplexes were analysed in non-denaturing PAGE. Direction of migration is marked by arrow.

The complete allelic profile of the family is not available. The patient (Lane 4) has inherited maternal allele B7 and paternal allele B44 at this locus. Father has B44 (slow) allele and an unidentified second allele; mother has B51 (slow) and B7 (fast) alleles. One sibling (lane 5) has identical B alleles with the patient.

Figure 6:
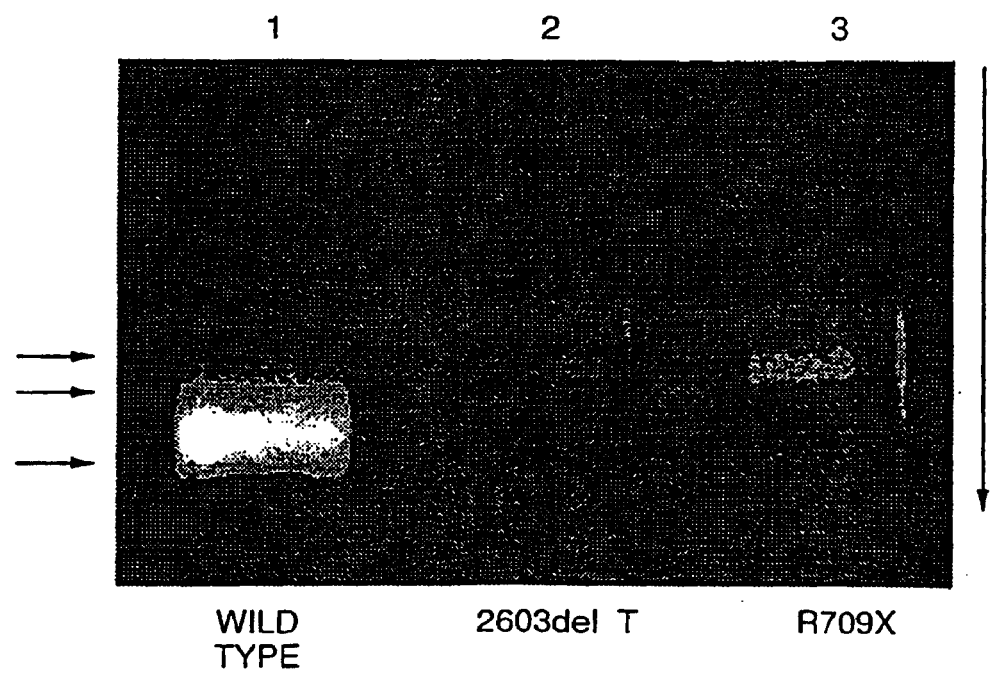

FIG. 6 illustrates the use of CSA to identify mutations in exon 13 of the cystic fibrosis gene.

DNA from a healthy individual and two cystic fibrosis patients were used to amplify exon 13 of the cystic fibrosis gene by PCR; single strand DNA was isolated and hybridised with complementary reference single strand wild type; the duplexes were analysed in non-denaturing PAGE.

Vertical arrow indicates direction of migration of bands; horizontal arrows point to the position of the bands.

The wild type in Lane 1 yields a single homoduplex (fast band). The patients have mutation in exon 13 and are heterozygous for this exon. The slow band in Lane 2 represents heteroduplex due to deletion of a single nucleotide (T) at position 2603 in the exon. In lane 3 the slow band is due to heteroduplex formation with the mutated allele R709X which differs from the wild type by a single substitution.

Figure 7:
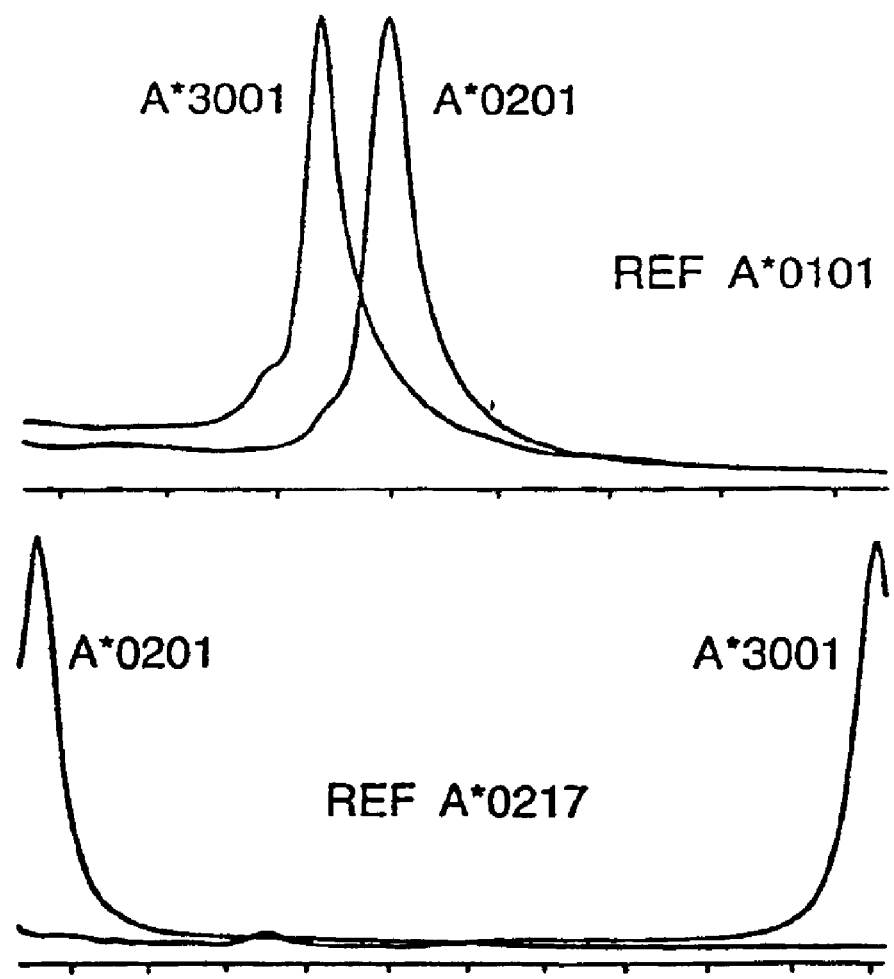

FIG. 7 shows fluorescent peaks observed in one embodiment of double strand conformation analysis (DSCA) and illustrates the use of two reference strands.

HLA-A 0201 and 3001 alleles from two samples were amplified and hybridised with two reference strands. The results in the upper box show duplex migration with reference A*0101 and the lower box with reference A*0217. The difference in the separation of the peaks is due to the number of nucleotide mismatches which affect the migration rates of the respective duplexes. This approach allows accurate identification of alleles which may have closely migrating bands that result in overlapping peaks with only one reference strand.

FIG. 8 shows the sensitivity of the DSCA method in the analysis of HLA-B and Cw alleles.

The upper box shows the analysis of HLA-B locus for cell line DAUDI. The fluorescent peaks detected distinguish between the two alleles B*5801 and B*5802 which differ by three nucleotides. The cell line WT49 is homozygous for B*5801 allele. The position of the peaks for B*5801 is identical irrespective of its source. The reference strand in this experiment was B*4402.

The lower box shows the analysis of the HLA-Cw locus from cell line CLA. This cell line is heterozygous for this locus and the alleles Cw*0701 and Cw*0702 differ by two nucleotides. The reference strand in this experiment was CW*0303.

Figure 9:
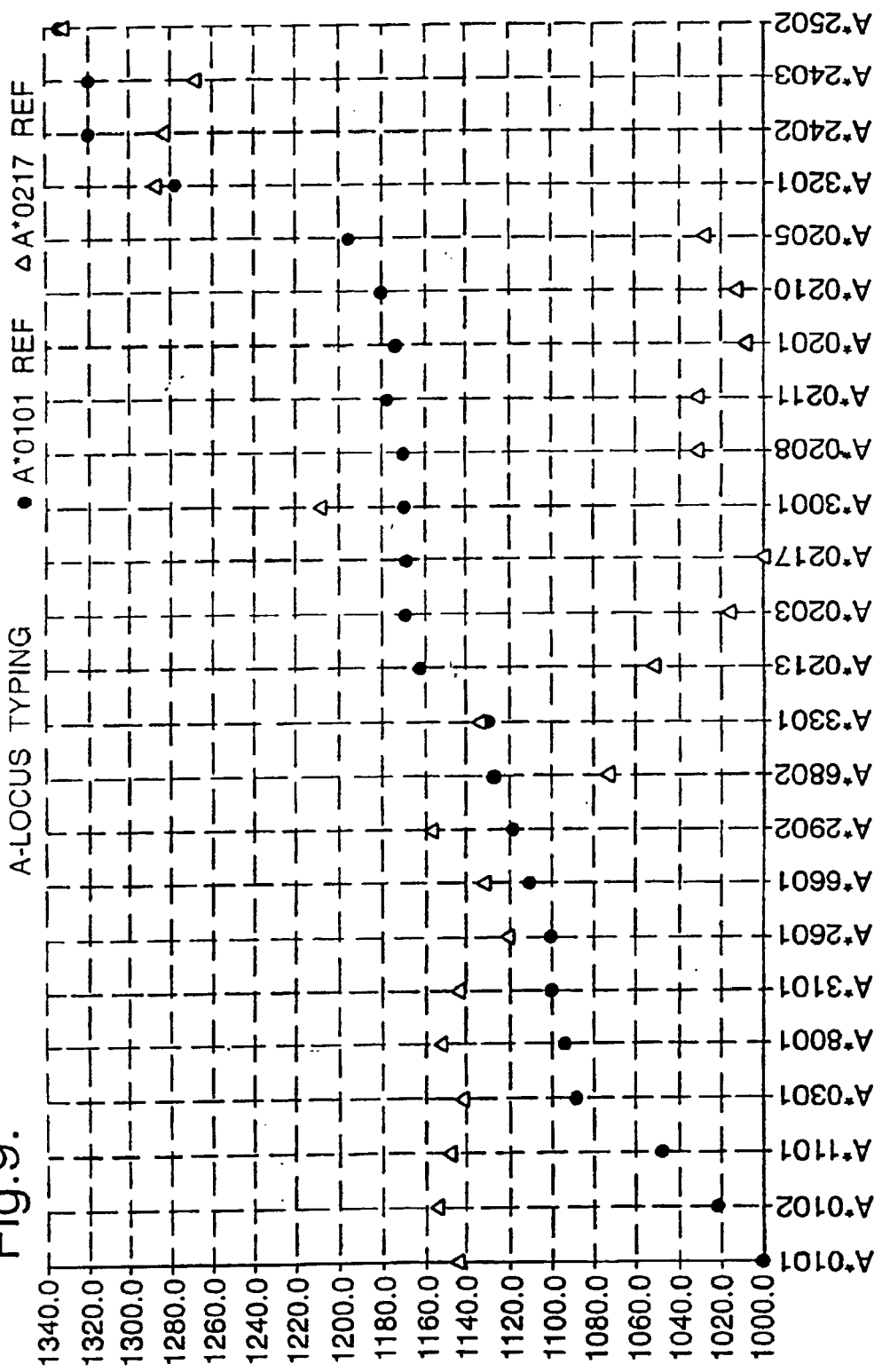
Figure 10:
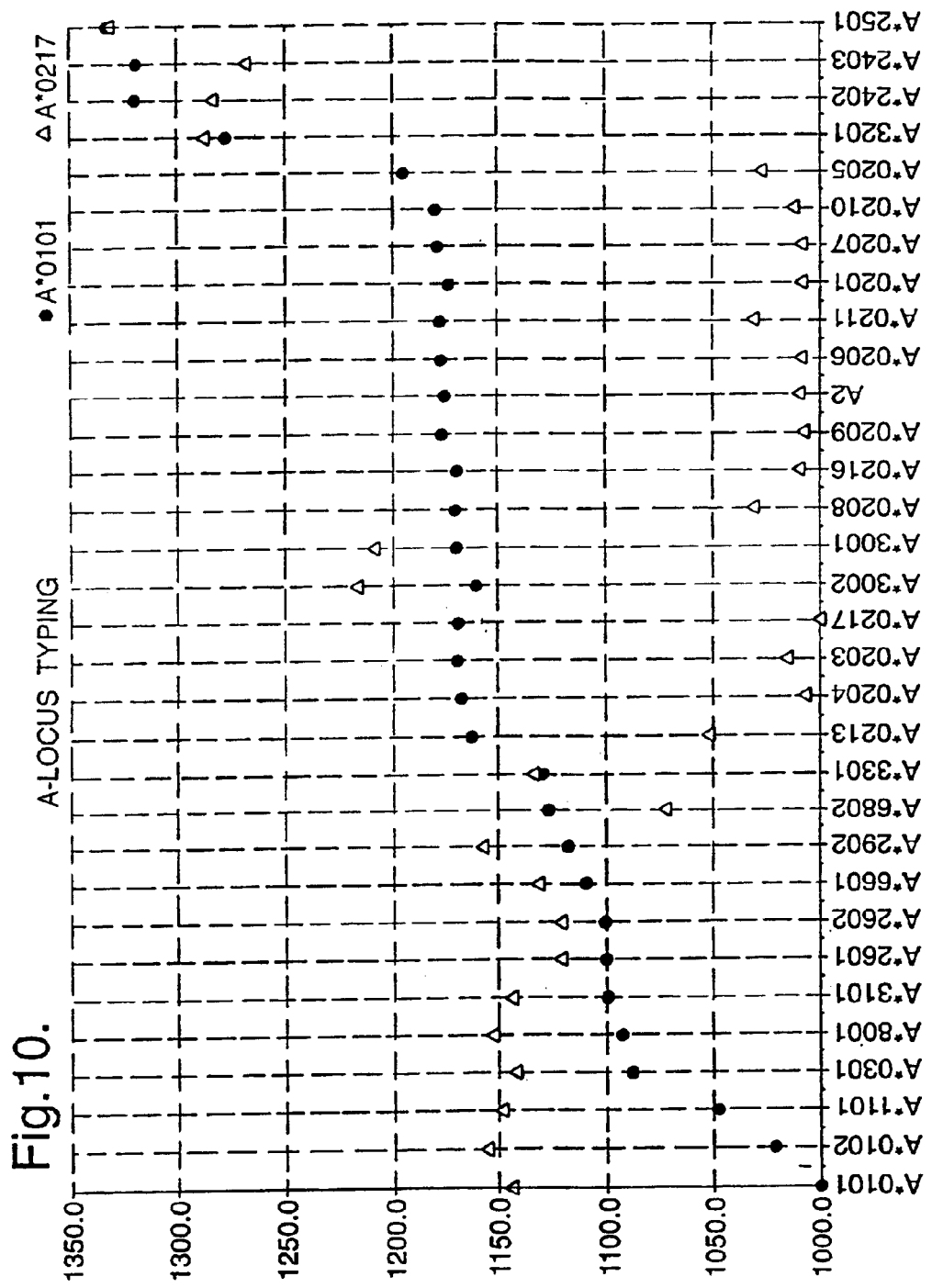

FIGS. 9 and 10 show the analysis of HLA-A alleles by DSCA using two reference strands. DNA was obtained from B-lymphoblastoid cell lines and amplified as described in Example 3. Hybridised duplexes were analysed by non-denaturing PAGE in an automated DNA sequencing instrument. Vertical axis indicates RV figure.

Figure 11:
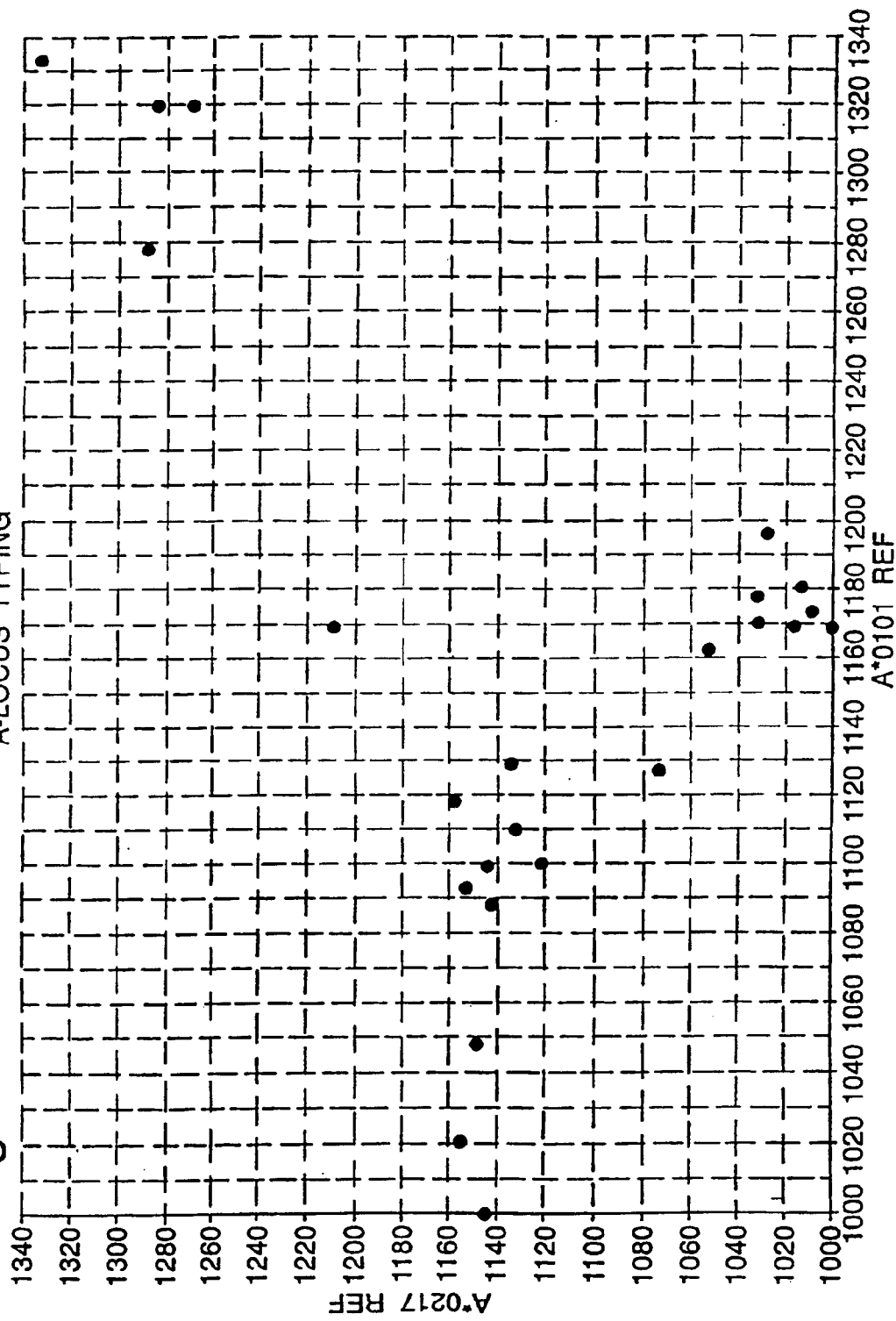

FIG. 11 shows a graphic analysis of the combined results from FIGS. 9 and 10. The plot of RV from the two reference strands allows unambiguous identification of the alleles typed by DSCA.

Figure 12:
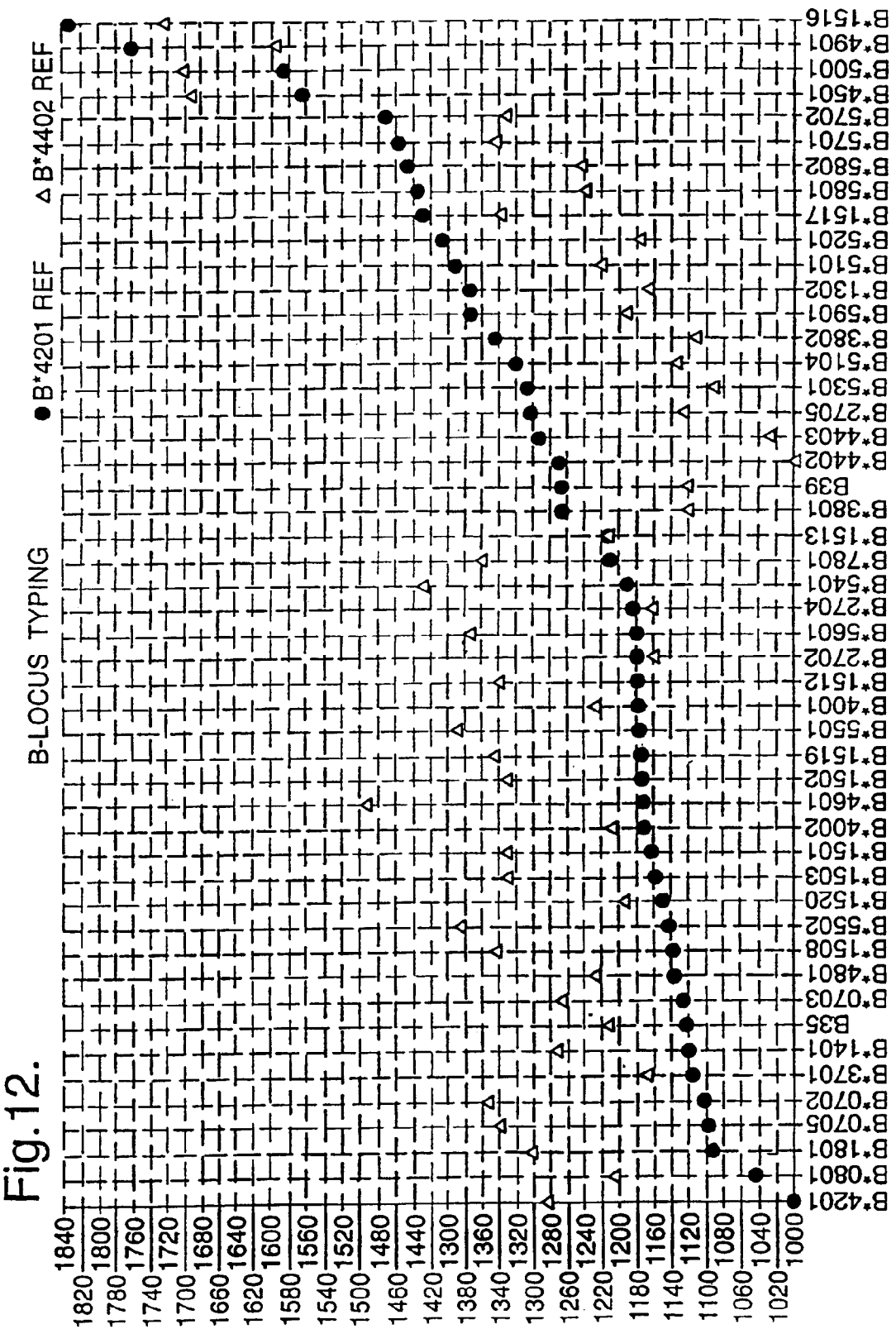
Figure 13:
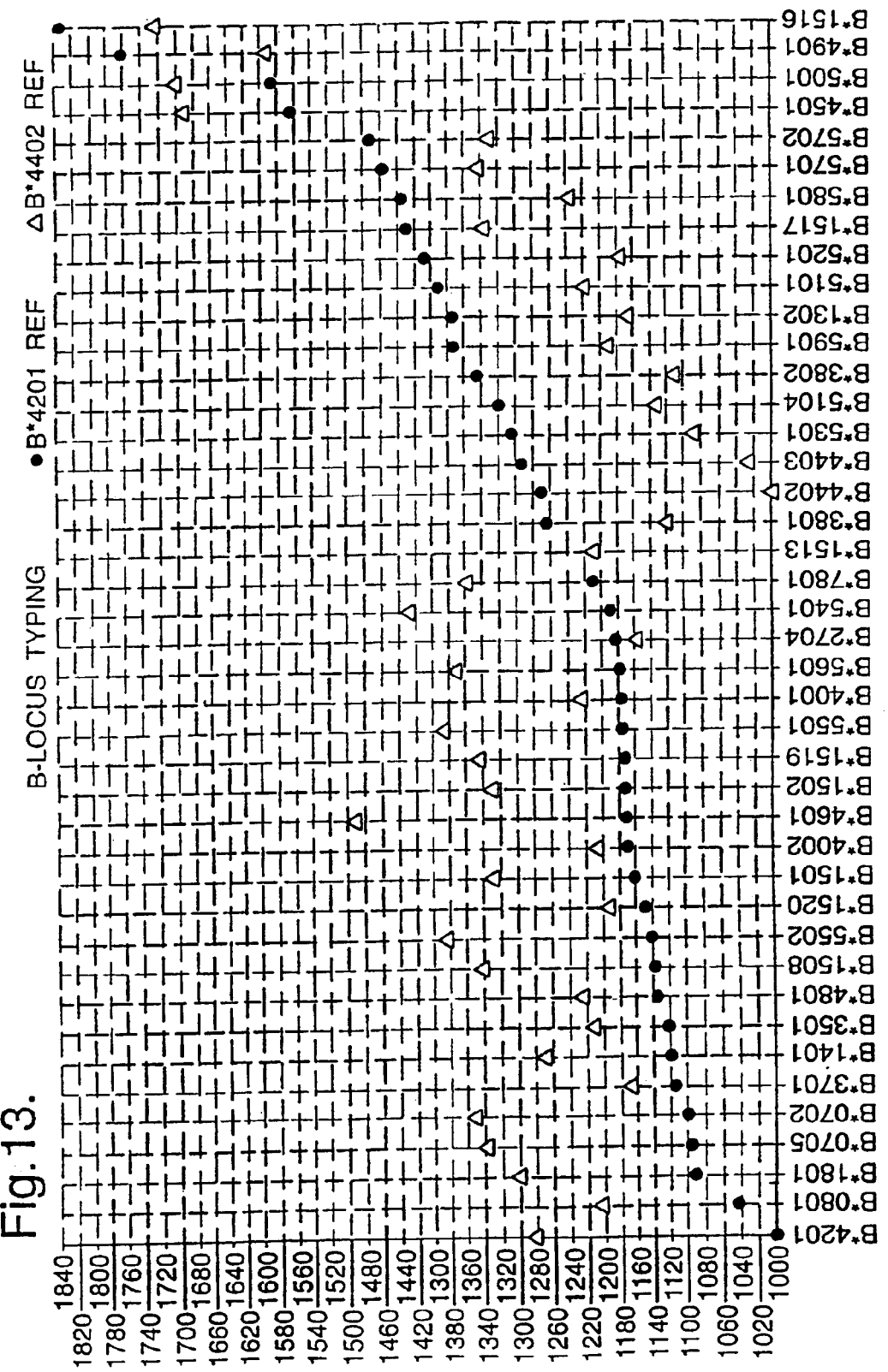

FIGS. 12 and 13 show the analysis of HLA-B alleles with the use of two reference strands. DNA was obtained from B-lymphoblastoid cell lines and amplified as described in Example 3. Hybridised duplexes were analysed by non-denaturing PAGE in an automated DNA sequencing instrument. Vertical axis indicates RV figure.

Figure 14:
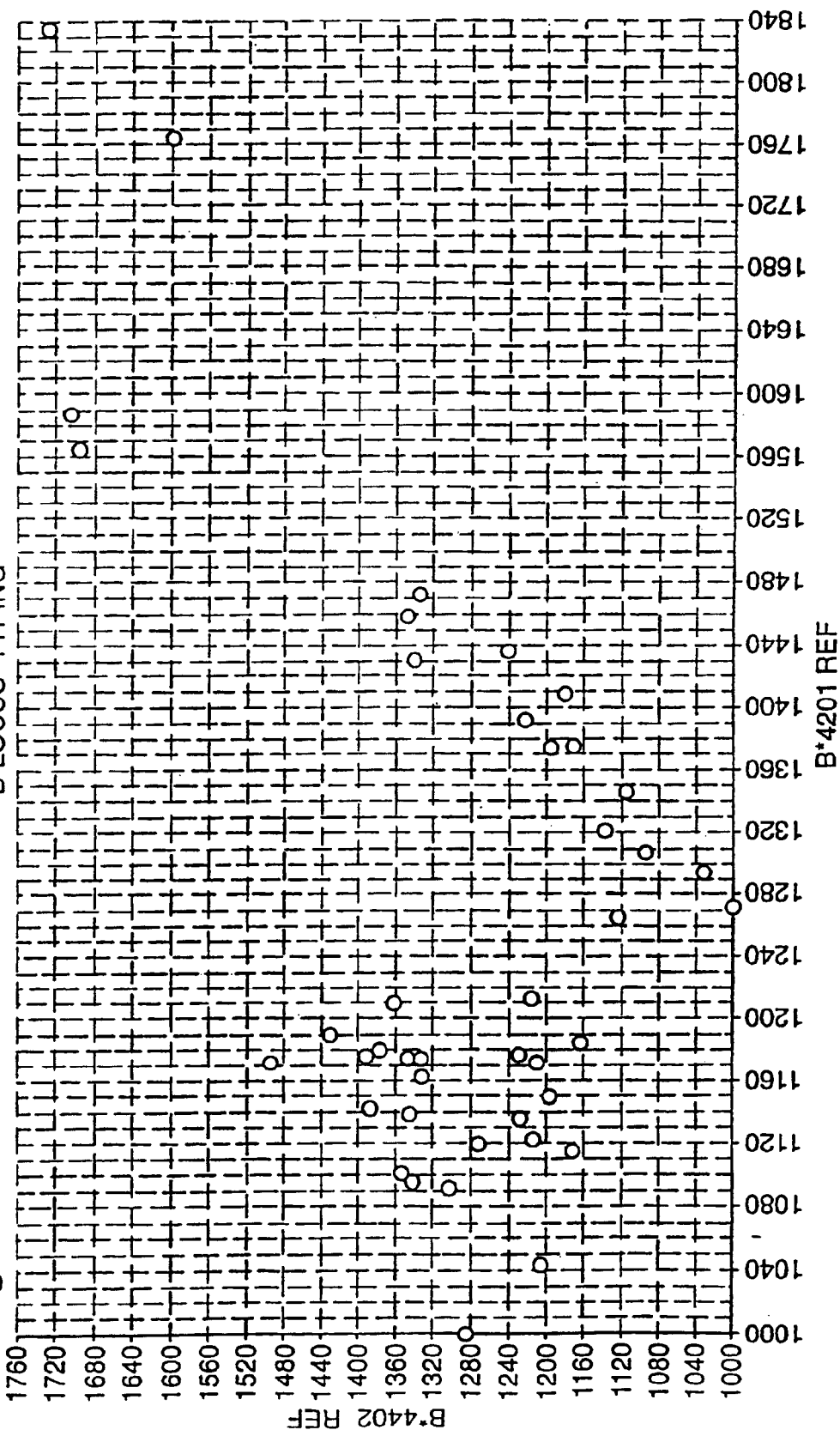

FIG. 14 shows a graphic analysis of the combined results from FIGS. 12 and 13. The RV plot from two reference strands permits the unambiguous identification of the alleles typed by DSCA.

Figure 15A:
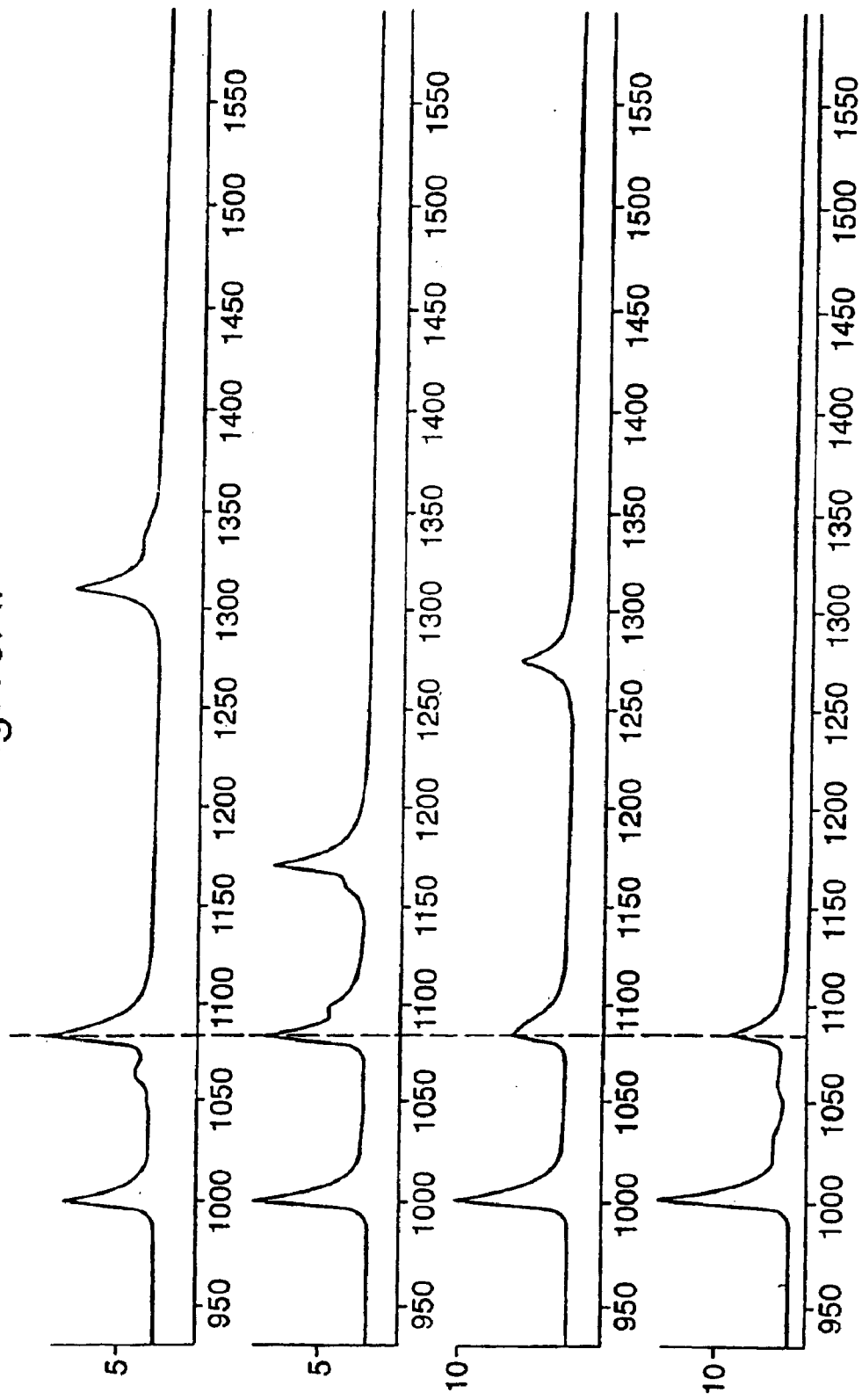
Figure 15B:
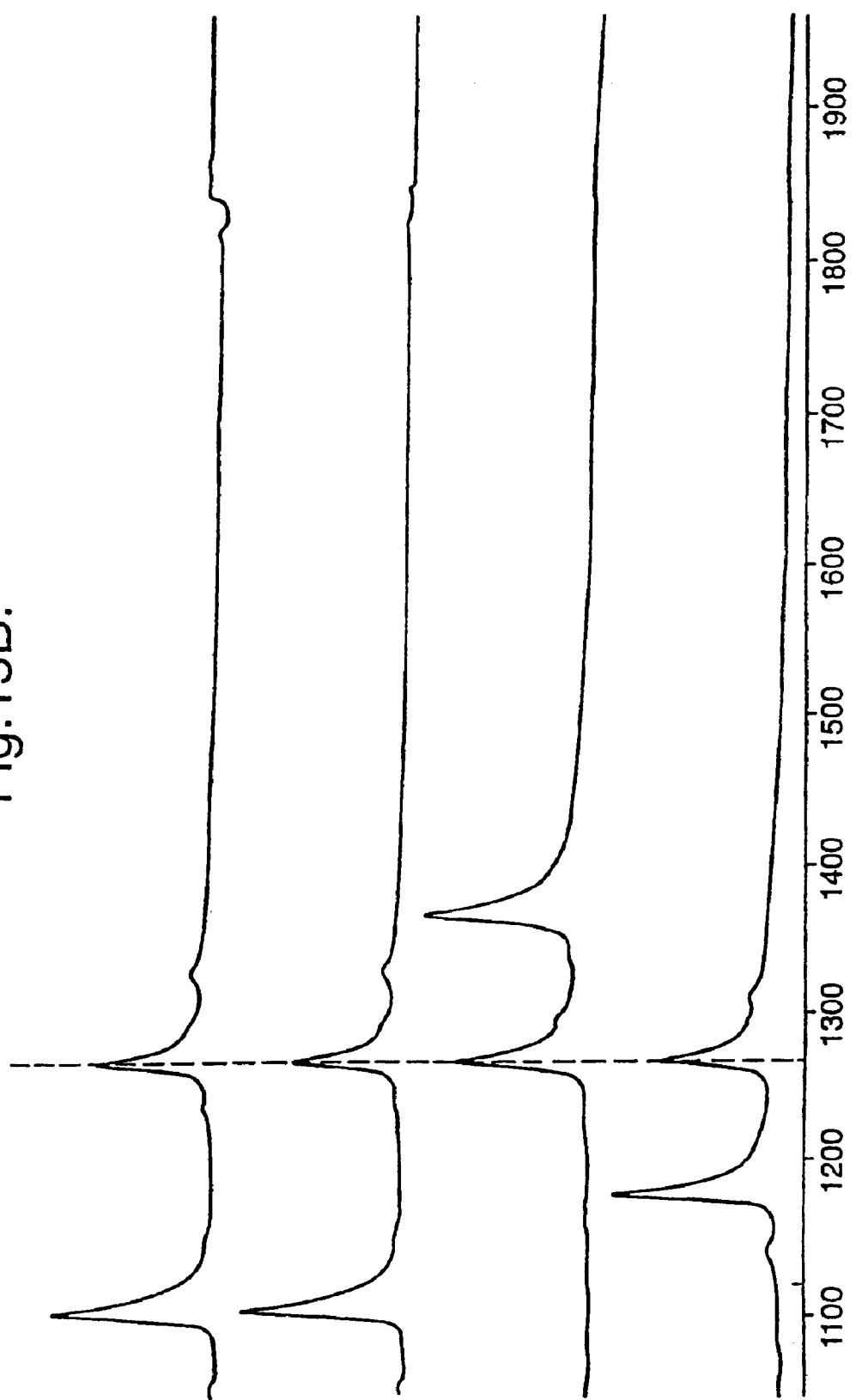

FIG. 15 illustrates the analysis by DSCA of four different samples for each of two alleles. In all cases the mobilities of the bands for each allele were identical. Box A shows the analysis of HMA*0301; the peak at RV 1000 is the homoduplex in this test run and additional peaks indicate heterozygosity of the relevant sample. Box B shows the analysis of HLA-B*4402; in this test run all four samples were heterozygous.

EXAMPLE 1

Seperation of HLA Allelic Strands by CSA

1. Methods
1.1 Summary

Amplification and isolation of the biotinylated anti-sense strand(s) were performed. They were then hybridised with allele specific reference sense single strands.

In order to test the resolving power of this method, 7 allele specific reference sense single strands were prepared. These were hybridised with several isolated anti-sense strand HLA-A alleles which were selected to include alleles with one or several nucleotide differences compared to the reference strand.

Following this step, PAGE analysis was performed under non-denaturing conditions (urea at a range of 2–6 M and formamide between 10%–30% concentrations were included in other experiments) and the gels were run at either room temperature or 50–58° C. (200 Volts for 6 hours).

The identification of a single band in PAGE gels indicated identity between the allele and the reference strand and homozygosity of the sample.

As a positive control, double strand DNA PCR product from the allele reference was always used.

1.2 Locus Specific Amplification of HLA Class I Genes

For typing purposes amplification of exons 2 and 3 is desirable, and the primers were therefore selected to amplify the stretch of the genome between intron 1 and intron 3. The localisation and nucleotide sequences of the HLA locus-specific primers used are given in the reagents section.

PCR reactions were performed in a total volume of 100 µl using 1 µg of genomic DNA and 25 pmoles of each locus-specific primer. The 3'-primer was biotinylated at 5'-end. This arrangement ensures the incorporation of the biotinylated primer onto the amplified antisense DNA strand. PCR conditions are given in the following table.

| Thermocycling conditions | | |
|---|---|---|
| A, B and C loci | | |
| 95° C. | 4 min. | 1 cycle |
| 95° C. | 30 sec. | |
| 65° C. | 50 sec. | 33 cycles |
| 72° C. | 30 sec. | |
| 72° C. | 8 min. | 1 cycle |

1.3 Separation of the Amplified DNA Strands
1.3a Removal of Non-Biotinylated Strand:

Magnetic beads with covalently coupled streptavidin on the surface were added to the PCR product and incubated for 30 minutes at 43° C. In this way the amplified PCR product was immobilised by the interaction of biotin and streptavidin. After incubation, the tubes were placed against a magnet and the beads were washed with washing buffer to remove the remaining PCR reaction components.

The non-biotinylated DNA strand was then dissociated from the beads by incubation with 0.15 M NaOH at room temperature (r.t.) for 10 minutes. Following this the beads were washed to remove excess NaOH and resuspended in 50 µl of hybridisation buffer.

1.3b Removal of Biotinylated DNA Strand:

The bead suspension was heated at 95° C. for 5 minutes; this ensures denaturation of the streptavidin molecule to release the biotinylated amplified anti-sense single strand which was then removed and placed in a clean tube. At this stage, the isolates contained single biotinylated DNA strands from each allele.

1.4 Preparation of Allele Specific Reference Single-Stranded DNA

DNA was extracted from 10th IHW cell lines. The following homozygous cell lines were selected:

| HLA-A | STEINLIN | (10th IHW) | A*0101 |
| HLA-B | SP0010 | (10th IHW) | B*4402 |
| HLA-Cw | STEINLIN | (10th IHW) | Cw*0701 |

The PCR conditions for amplification were as above, with the exception that in each case the locus-specific 5'-primer was biotinylated (5'-end). The PCR products were analysed by PAGE to assess the fidelity of the amplification and in all cases a single band was obtained.

1.5 Hybridisation

The biotinylated anti-sense strand(s) from above were mixed with the sense strands, and the mixture was heated at 95° C. for 3 min., incubated at 70° C. for 5 min., and then at 65° C. for 45 min. Under these conditions, the sense and anti-sense strands were optimally hybridised and produced good yields. The heteroduplexes formed could subsequently be separated from each other by electrophoresis in polyacrylamide gel.

2. Reagents:

A) Nucleotide Sequences of Primers Used for Locus-Specific Amplification:

5' A locus primer: (SEQ ID NO:1)
GAA ACG/C GCC TCT GT/CG GGG AGA AGC AA
(Intron 1: 21–46)

3' A locus primer: (SEQ ID NO:2)
TGT TGG TCC CAA TTG TCT CCC CTC
(Intron 3: 66–89)

5' B locus primer: (SEQ ID NO:3)
GGG AGG AGC GAG GGG ACC G/CCA G
(Intron 1: 36–57)

3' B locus primer: (SEQ ID NO:4)
GGA GGC CAT CCC CGG CGA CCT AT
(Intron 3: 37–59)

5' C locus primer: (SEQ ID NO:5)
AGC GAG GG/TG CCC GCC CGG CGA
(Intron 1: 42–61)

-continued

3' C locus primer:  (SEQ ID NO:6)
GGA GAT GGG GAA GGC TCC CCA CT
(Intron 3: 12–35)

B) Buffers:

| Washing buffer: | 10 mM | Tris-HCl pH 7.5 |
| | 1.0 mM | EDTA |
| | 2.0 M | NaCl (or 6 M LiCl) |
| Hybridisation buffer: | 20 mM | Tris-HCl pH 8.4 |
| | 50 mM | KCl |
| PCR buffer: | 20 mM | Tris-HCl pH 8.4 |
| | 50 mM | KCl |
| | 0.2 mM | MgCl2 |
| TE buffer | 10 mM | Tris-HCl pH 7.5 |
| | 1 mM | EDTA |

C) Various
   Dynabeads M-280 Streptavidin* (10 mg/ml)
   Magnetic particle concentrator-Dynal MPC
   A Thermal cycler (PTC-200 Peltier Thermal Cycler MJ Research*)
   Ultrapure dNTP set, 2'-Deoxynucleoside 5'-Triphosphate (Pharmacia Biotech)
   Taq DNA PolyTmerase* (various commercial sources)
   50 mM MgCl2
   0.15 M NaOH
   SeaPlaque Agarose* (Flowgen Instruments Ltd)
   Long Ranger 50% acrylamide (Flowgen)
   *=Trade Names 3. Results: Identification of Alleles by CSA Seven allele specific reference sense strands were isolated from homozygous cell lines and hybridised to several anti-sense strands from other cell lines whose HLA specificity was defined by sequencing and in some cases only by serology.

Allelic bands could be identified by homoduplex formation with a reference strand, which would migrate at the same rate as the double stranded DNA reference band (control band) or heteroduplex bands, cathodic compared with the control band.

Figure 1:
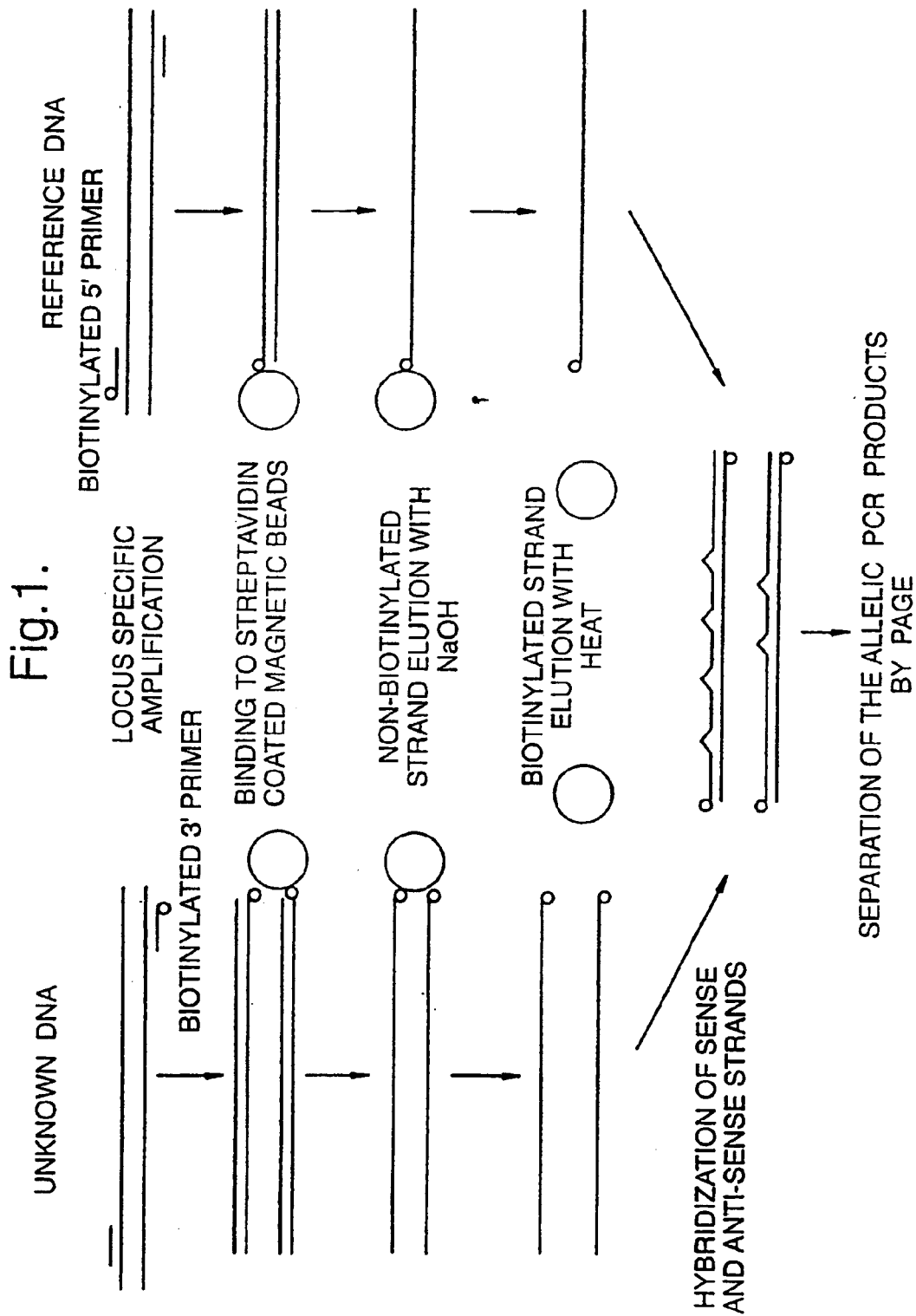
FIG. 1 shows a schematic overview of an embodiment of the invention.
Figure 2:
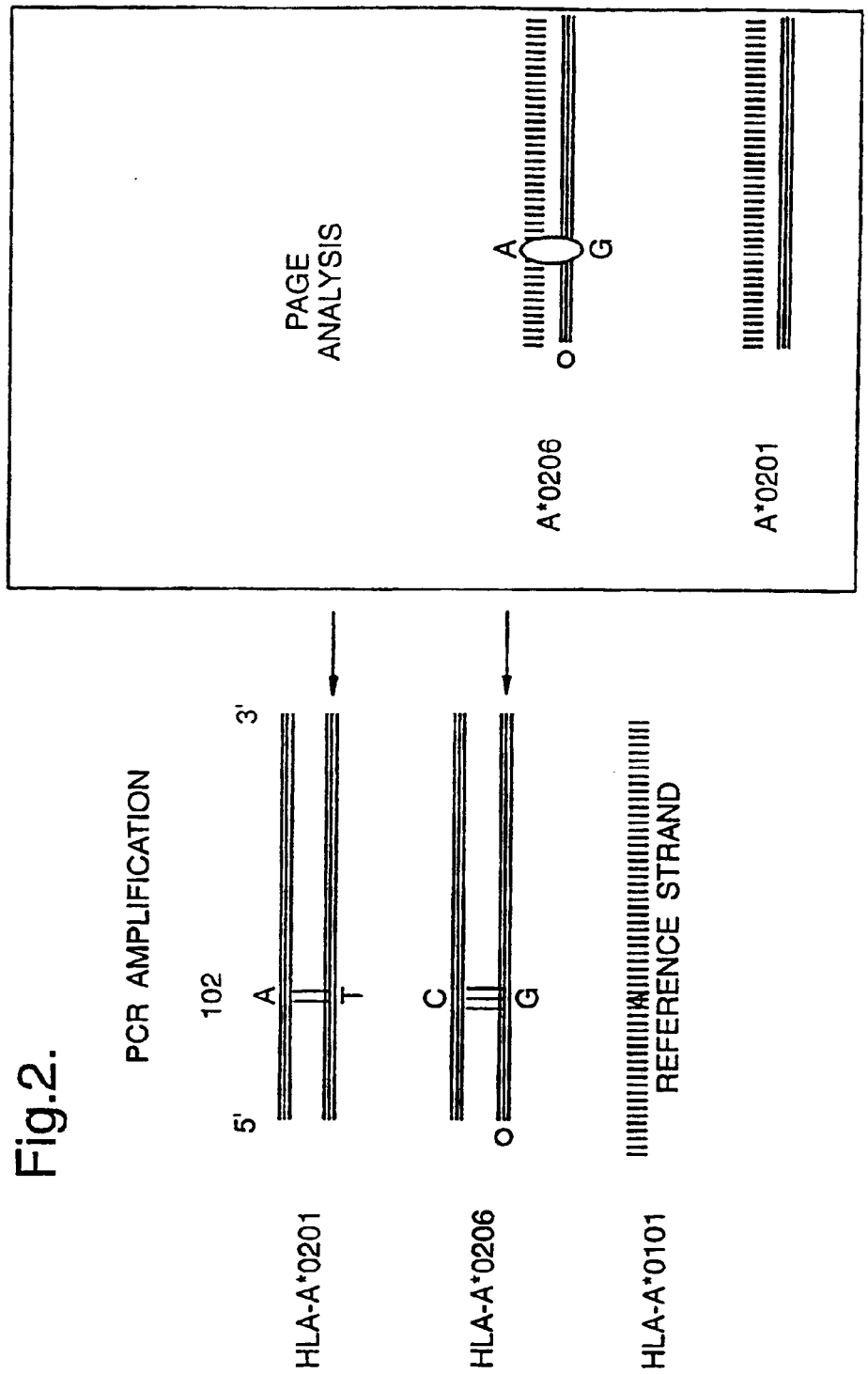
FIG. 2 shows a schematic overview of another embodiment the invention. The difference in alleles A*0201 and A*0206 is one nucleotide at position 102 on exon 2. The reference strand has adenine at that position and there are other differences the reference and the sample sequences. Sense or antisense DNA strands may be used providing that the base sequence of reference DNA is complementary to the unknown sample DNA.
Figure 3:
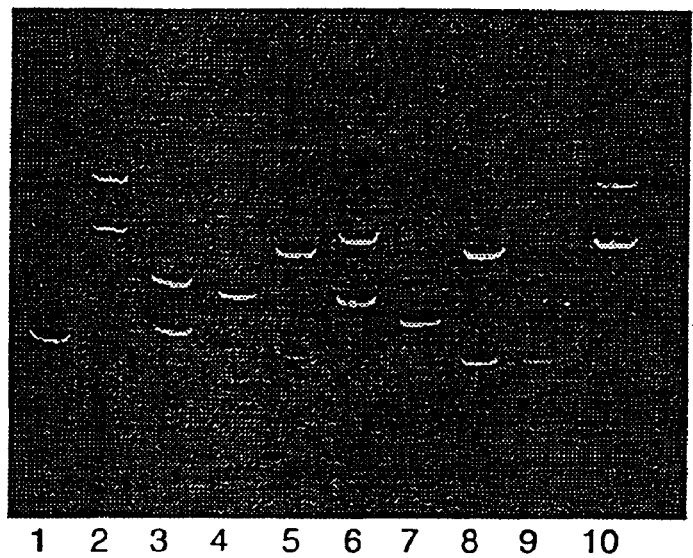
FIG. 3 shows the band pattern on gel electrophoresis between the sense reference strand of the allele HLA-A*0101 and anti-sense strands from several locus A alleles. Lane 1: STEINLIN (A*0101), Lane 2: KIME (A*0211–A*3201), Lane 3: DAUDI (A*0102–A*6601), Lane 4: EA (A*0301), Lane 5: LCL721 (A*0101–A*0201), Lane 6: M7 (A*0202–A0301), Lane 7: CJO-A (A*1101), Lane 8: T5-1 (A0101–A*0201), Lane 9: L0541265 (A*0101), Lane 10 AM (A*0205–A3201).

It was observed that when the reference strand matched completely the anti-sense strand a single homoduplex band was visible in the gel. In cases when the reference strand differed by 3 or more bases from the anti-sense strand, a cathodic band corresponding to a heteroduplex was seen. This pattern was observed reproducibly for all the allele specific reference strands and is therefore independent of the position of the mismatch(es) on the strands and the specific base sequence of the allelic reference (FIG. 3).

In other experiments with longer PAGE it was possible to separate allelic strands that were different by only a single nucleotide. Use of denaturing PAGE enhanced the separation of the allelic bands.

This method of allele separation has been used to analyse HLA-A, HLA-B and HLA-Cw alleles from 22 heterozygous and 41 homozygous cell lines (HLA-A 33; HLA-B 30 and HLA-Cw 18 alleles) and to identify the individual alleles without ambiguity by a method named "URSTO" and described in ref 35 and in an international (PCT) patent application being filed on the same day as this application in the name of the Anthony Nolan Bone Marrow Trust. In particular DNA was extracted from 63 B-lymphoblastoid cell lines, which included 22 heterozygous and 41 homozygous lines. After PCR amplification with locus specific primers the anti-sense single strands were isolated and hybridised with the appropriate reference strands (A*0101, B*4402, Cw*0701). The allelic bands were resolved in non-denaturing PAGE and eluted from low melting point agarose. Alleles were identified unambiguously from the isolated DNA. The particular alleles isolated are set out in the following Table.

TABLE 1

HLA CLASS I ALLELES ISOLATED BY COMPLEMENTARY STRAND ANALYSIS

| HLA-A (n = 33) | | | | | | |
|---|---|---|---|---|---|---|
| A*0101, | A*0102, | A*0201, | A*0202, | A*0203, | A*0204, | A*0205 |
| A*0206, | A*0207, | A*0208, | A*0209, | A*0210, | A*0211, | A*0212, |
| A*0213, | A*0216, | A*0217, | A*0301, | A*1101, | A*2301, | A*2402, |
| A*2403, | A*2501, | A*2601, | A*2902, | A*3001, | A*3002, | A*3101, |
| A*3201, | A*3301, | A*6601, | A*6602, | A*6802. | | |
| HLA-B (n = 30) | | | | | | |
| B*0702, | B*0801, | B*1302, | B*1402, | B*1501, | B*1502, | A*1520, |
| B*1801, | B*3501, | B*3701, | B*3801, | B*4001, | B*4002, | B*4101, |
| B*4201, | B*4402, | B*4403, | B*4601, | B*4701, | B*4801, | B*4901, |
| B*5001, | B*5101, | B*5201, | B*5301, | B*5502, | B*5701, | B*5801, |
| B*5802, | B*6701. | | | | | |
| HLA-Cw (n = 18) | | | | | | |
| Cw*0102, | Cw*0202, | Cw*0302, | Cw*0303, | Cw*0304, | Cw*0401, | |
| Cw*0501, | Cw*0602, | Cw*0701, | Cw*0702, | Cw*0704, | Cw*0802, | |
| Cw*1202, | Cw*1203, | Cw*1402, | Cw*1502, | Cw*1601, | Cw*1701. | |

Number of different heterozygous combinations tested: HLA-A 19, HLA-B 14, and HLA-Cw 11.

In further experiments, it was shown that heteroduplexes of the same alleles from different sources migrate to the same position on the gel. FIG. 3 shows the results from such an experiment. Lanes 1, 5 and 8 contain duplexes comprising A0101 from different sources and the duplexes all migrated to the same position. Lanes 5 and 8 also contain duplexes comprising A0201 from different sources and these migrated at the same speed, but more slowly than the A0101 duplexes.

This reproducible mobility of allelic bands can be used as a method for the identification of alleles diagnostically.

EXAMPLE 2

Seperation of EXON 13 Mutations of Cystic Fibrosis Gene

CSA can be used for the isolation of any polyallelic gene. This example shows the analysis of the cystic fibrosis gene. The largest encoded exon of this gene is exon 13. Samples from an unaffected individual which is homozygous for the wild type exon 13 and samples from two mutations were prepared and analysed by CSA. The mutation samples were from individuals with a single base deletion 2603delT[36] and a single nucleotide substitution at position 709–R709X [37]. These samples had previously been typed by other methods.

PCR amplification of the exon 13 of the cystic fibrosis gene was performed as described in Zielenski et al[38] except that the 5' primer was biotinylated at the 5' end. The reference strand was prepared from the wild type sample and after the preparation of the single strands from three samples as described in example 1, these were hybridised with the reference strand and analysed in non-denaturing PAGE. The result is shown in FIG. 6. The mutations result in chimeric duplexes which result in retardation of the mutated allelic bands in the gel (see lanes 2 and 3) compared to the wild type homoduplex (see lane 1).

EXAMPLE 3

Allelic Identification by Double Strand Conformation Analysis (DSCA)

This Example shows how DNA fragments from a particular segment of a genome can be analysed and identified using a labelled reference strand without isolation of the duplex from the analysis phase. The Example uses specific reference strands for HLA-A, B and Cw alleles.

The reference strands were prepared using sense primers for the three loci, which had fluorescent dye (Pharmacia Ltd) at the 5'-end. These were not biotinylated. Separate PCR reactions were performed for each locus to produce the reference reagents. The primer sequences and PCR conditions were as described above in Example 1 and the amplified reference strands included exons 2 and 3, intron 2 and short segments from introns 1 and 3 of each locus. Lymphoblastoid, homozygous cell lines were used for each locus amplification and a number of reference strands were tested in order to obtain optimum separation and least ambiguity in the identification of the relevant alleles (see FIG. 7 and Table 2 below). For analysis of the HLA class I alleles, the use of two reference strands for each locus allows optimum differentiation between the alleles tested. FIG. 8 illustrates the resolution of the DSCA method.

TABLE 2

DOUBLE STRAND CONFORMATION ANALYSIS TESTING OF REFERENCE STRANDS

| | Allele | RV | No tested | RV | No tested |
|---|---|---|---|---|---|
| | | REF: A*0101 | | REF: A*0217 | |
| A-locus | A*0201 | 1169.0 ± 0.71 | 9 | 1009.4 ± 0.52 | 8 |
| | A*0301 | 1085.5 ± 0.55 | 6 | 1143.7 ± 1.03 | 6 |
| | A*2402 | 1308.8 ± 0.45 | 5 | 1291.7 ± 0.76 | 7 |
| | A*3001 | 1168.0 ± 0.71 | 5 | 1210.0 ± 0.0 | 2 |

TABLE 2-continued

DOUBLE STRAND CONFORMATION ANALYSIS TESTING OF REFERENCE STRANDS

| | Allele | RV | No tested | RV | No tested |
|---|---|---|---|---|---|
| | | REF: B*4201 | | REF: B*4402 | |
| B-locus | B*0801 | 1044.0 ± 0.0 | 5 | 1204.0 ± 0.0 | 3 |
| | B*1302 | 1373.7 ± 0.58 | 4 | 1171.7 ± 0.58 | 3 |
| | B*1501 | 1164.8 ± 0.50 | 4 | 1331.5 ± 1.00 | 4 |
| | B*4001 | 1179.0 ± 0.0 | 4 | 1230.0 ± 1.00 | 3 |
| | B*3801 | 1264.0 ± 0.0 | 3 | 1124.3 ± 0.50 | 4 |
| | B*4403 | 1296.7 ± 0.58 | 3 | 1031.3 ± 0.58 | 4 |
| | B*5101 | 1392.5 ± 0.58 | 4 | 1221.6 ± 0.89 | 5 |
| | | REF: Cw*0303 | | REF: Cw*0701 | |
| Cw-locus | Cw*0401 | 1131.5 ± 0.58 | 4 | 1432.8 ± 0.50 | 4 |
| | Cw*0501 | 1063.2 ± 0.84 | 5 | 1399.7 ± 0.58 | 3 |
| | Cw*0602 | 1075.8 ± 0.40 | 11 | 1377.8 ± 0.45 | 5 |
| | Cw*0701 | 1782.8 ± 0.50 | 4 | (reference) | |

RV=relative value, is the measure of the migration of the bands. It is arrived at by using the positions of the front running primer band and the reference homoduplex (values 1 and 1000 respectively) in each track, to compute a stranded curve. The values of the migration of the subsequent bands are calculated from this curve. RV is followed by SD for each set of tests.

DNA samples were prepared in the same manner from other cell lines using non-biotinylated locus specific primers. The amplified sample and the reference preparation were mixed in a ratio of 2:1 or 3:1 and hybridised (as in item 2.5 of Example 1) and applied to 6% non-denaturing PAG (Long Ranger, Trade Name). The electrophoretic analysis was performed in an ALFexpress DNA sequencer™ (Pharmacia Ltd) and the mobilities of the labelled duplexes were determined with an integral laser activated system with photodiode detectors. The results are shown in FIGS. 9–14 and in the following Table.

TABLE 3

HLA-A LOCUS

| ALLELE | REFERENCE RV | A*0101 No tested | REFERENCE RV | A*0217 No tested |
|---|---|---|---|---|
| A*0101 | 1000 | (reference) | 1144.0 ± 6.4 | 24 |
| A*0102 | 1020.6 ± 0.7 | 9 | 1154.8 ± 2.9 | 4 |
| A*1101 | 1047.8 ± 1.1 | 9 | 1148.3 ± 3.0 | 8 |
| A*0301 | 1087.8 ± 1.9 | 23 | 1142.0 ± 5.2 | 36 |
| A*8001 | 1092.8 ± 2.0 | 8 | 1152.6 ± 2.9 | 5 |
| A*3101 | 1099.3 ± 2.2 | 13 | 1143.9 ± 3.5 | 14 |
| A*2601 | 1100.0 ± 2.4 | 10 | 1121.2 ± 2.3 | 5 |
| A*6601 | 1109.6 ± 2.8 | 17 | 1131.6 ± 2.5 | 11 |
| A*2902 | 1117.6 ± 2.1 | 8 | 1157.1 ± 3.3 | 8 |
| A*6802 | 1126.9 ± 2.8 | 9 | 1073.0 ± 1.0 | 5 |
| A*3301 | 1129.0 ± 2.7 | 18 | 1133.7 ± 5.0 | 12 |
| A*0213 | 1162.1 ± 3.3 | 10 | 1052.0 ± 1.7 | 4 |
| A*0203 | 1168.9 ± 3.3 | 8 | 1016.0 ± 1.2 | 4 |
| A*0217 | 1168.5 ± 3.1 | 8 | 1000 | (reference) |
| A*3001 | 1169.3 ± 3.3 | 30 | 1208.7 ± 6.0 | 19 |
| A*0208 | 1170.0 ± 3.7 | 9 | 1031.3 ± 0.5 | 4 |
| A*0201 | 1173.5 ± 5.1 | 13 | 1008.8 ± 1.4 | 22 |
| A*0211 | 1177.7 ± 4.7 | 10 | 1031.5 ± 3.1 | 4 |
| A*0210 | 1180.2 ± 3.4 | 9 | 1013.0 ± 0.8 | 4 |
| A*0205 | 1195.6 ± 4.9 | 10 | 1027.8 ± 0.8 | 6 |
| A*3201 | 1278.1 ± 7.6 | 20 | 1288.4 ± 6.8 | 20 |
| A*2402 | 1320.1 ± 8.5 | 22 | 1284.2 ± 6.3 | 39 |

TABLE 3-continued

| | | | | |
|---|---|---|---|---|
| A*2403 | 1320.0 ± 6.5 | 4 | 1268.9 ± 5.2 | 9 |
| A*9501 | 1333.5 ± 7.3 | 8 | 1333.0 ± 3.8 | 4 |

HLA-B LOCUS

| ALLELE | REFERENCE RV | B*4201 No tested | REFERENCE RV | B*4402 No tested |
|---|---|---|---|---|
| B*4201 | 1000 | (reference) | 1284.2 ± 2.8 | 10 |
| B*0801 | 1043.2 ± 0.9 | 21 | 1206.1 ± 3.0 | 15 |
| B*1801 | 1092.0 ± 1.5 | 5 | 1302.0 ± 4.9 | 7 |
| B*0705 | 1096.3 ± 1.0 | 4 | 1341.0 ± 3.9 | 4 |
| B*0702 | 1100.7 ± 0.8 | 6 | 1353.9 ± 3.6 | 7 |
| B*3701 | 1115.0 ± 3.2 | 4 | 1170.6 ± 2.0 | 7 |
| B*1401 | 1120.3 ± 1.7 | 4 | 1272.2 ± 1.6 | 5 |
| B*3501 | 1122.1 ± 2.2 | 28 | 1213.6 ± 2.6 | 28 |
| B*4801 | 1136.3 ± 3.1 | 4 | 1227.8 ± 3.2 | 5 |
| B*1508 | 1138.8 ± 2.2 | 4 | 1344.4 ± 4.9 | 5 |
| B*5502 | 1142.4 ± 2.9 | 5 | 1387.3 ± 3.8 | 6 |
| B*1520 | 1149.7 ± 3.1 | 9 | 1195.8 ± 3.0 | 11 |
| B*1501 | 1162.8 ± 2.8 | 19 | 1331.7 ± 4.5 | 21 |
| B*4002 | 1171.7 ± 4.9 | 4 | 1209.8 ± 3.7 | 5 |
| B*4601 | 1172.3 ± 3.0 | 4 | 1495.0 ± 3.0 | 4 |
| B*1502 | 1174.0 ± 4.1 | 5 | 1332.1 ± 2.7 | 7 |
| B*1519 | 1174.3 ± 3.6 | 4 | 1347.0 ± 3.6 | 4 |
| B*5501 | 1176.3 ± 1.0 | 4 | 1390.5 ± 0.7 | 4 |
| B*4001 | 1176.8 ± 3.1 | 25 | 1229.0 ± 2.3 | 22 |
| B*5601 | 1180.0 ± 1.8 | 4 | 1375.5 ± 3.5 | 4 |
| B*2704 | 1184.8 ± 3.3 | 4 | 1162.8 ± 2.2 | 5 |
| B*5401 | 1190.5 ± 3.0 | 4 | 1430.5 ± 7.8 | 4 |
| B*7801 | 1211.3 ± 3.3 | 4 | 1362.3 ± 5.0 | 4 |
| B*1513 | 1213.0 ± 1.8 | 4 | 1215.4 ± 3.0 | 7 |
| B*3801 | 1265.7 ± 2.5 | 18 | 1123.1 ± 3.0 | 20 |
| B*3901 | 1267.2 ± 2.7 | 5 | 1124.5 ± 3.5 | 4 |
| B*4402 | 1271.3 ± 3.5 | 10 | 1000 | (reference) |
| B*44031 | 1293.9 ± 3.8 | 18 | 1030.7 ± 1.7 | 14 |
| B*5301 | 1307.5 ± 2.1 | 6 | 1093.6 ± 2.4 | 7 |
| B*5104 | 1321.5 ± 4.0 | 4 | 1136.8 ± 2.2 | 4 |
| B*3802 | 1346.0 ± 3.5 | 4 | 1114.9 ± 2.0 | 7 |
| B*5901 | 1374.5 ± 1.3 | 4 | 1194.8 ± 2.6 | 4 |
| B*1302 | 1375.0 ± 6.0 | 18 | 1169.6 ± 3.0 | 18 |
| B*5101 | 1392.7 ± 4.7 | 20 | 1222.8 ± 2.4 | 24 |
| B*5201 | 1408.8 ± 5.3 | 6 | 1179.9 ± 2.9 | 7 |
| B*1517 | 1431.3 ± 5.9 | 4 | 1340.5 ± 4.8 | 4 |
| B*5801 | 1436.9 ± 5.3 | 11 | 1241.0 ± 15.9 | 9 |
| B*5701 | 1459.1 ± 5.8 | 10 | 1347.4 ± 13.9 | 12 |
| B*5702 | 1473.3 ± 4.6 | 4 | 1334.8 ± 3.2 | 4 |
| B*4501 | 1566.3 ± 5.9 | 4 | 1696.5 ± 14.8 | 4 |
| B*5001 | 1588.5 ± 5.6 | 13 | 1705.2 ± 4.2 | 6 |
| B*4901 | 1764.5 ± 12.8 | 6 | 1598.5 ± 12.1 | 4 |
| B*1516 | 1836.3 ± 5.9 | 4 | 1727.8 ± 6.4 | 5 |

HLA-Cw LOCUS

| | | | | |
|---|---|---|---|---|
| Cw*0701 | 1000 | (reference) | 1782.8 ± 0.5 | 4 |
| Cw*0702 | 1019.4 ± 1.4 | 8 | 1824.6 ± 8.8 | 5 |
| Cw*0704 | 1042.3 ± 0.6 | 4 | 1807.3 ± 3.6 | 4 |
| Cw*0302 | 1341.5 ± 6.4 | 4 | 1029.3 ± 1.0 | 4 |
| Cw*1601 | 1350.6 ± 2.3 | 7 | 1048.9 ± 1.8 | 7 |
| Cw*0303 | 1351.9 ± 5.0 | 7 | 1000 | (reference) |
| Cw*0102 | 1376.2 ± 6.2 | 13 | 1074.3 ± 1.5 | 6 |
| Cw*0602 | 1376.4 ± 7.0 | 28 | 1075.6 ± 1.1 | 18 |
| Cw*0801 | 1377.5 ± 1.3 | 4 | 1059.3 ± 1.3 | 7 |
| Cw*1202 | 1380.0 ± 5.7 | 4 | 1064.3 ± 1.1 | 7 |
| Cw*1203 | 1387.5 ± 7.6 | 10 | 1065.9 ± 1.5 | 7 |
| Cw*1402 | 1392.5 ± 2.6 | 4 | 1067.3 ± 1.1 | 7 |
| Cw*1502 | 1394.3 ± 8.3 | 4 | 1060.4 ± 1.5 | 7 |
| Cw*0501 | 1395.8 ± 5.0 | 1 | 1063.2 ± 2.5 | 13 |
| Cw*0401 | 1428.8 ± 6.4 | 4 | 1131.4 ± 2.0 | 13 |
| Cw*1701 | 1436.0 ± 9.4 | 5 | 1076.5 ± 3.0 | 4 |

The analysis of the combined data from two reference strands is demonstrated in FIG. 11 for HLA-A and in FIG. 14 for HLA-B locus. In this graphic analysis, the RV for one reference strand is plotted against the RV of a second reference. This results in a unique parameter for each allele that is diagnostic for each allele tested.

EXAMPLE 4

DSCA Analysis of Intron 2 Sequences from HLA Class I Alleles

It is generally agreed that the extensive polymorphism of the HLA alleles is confined mainly to the antigen recognition sites. These are encoded for by exons 2 and 3 of the HLA class I genes. This segment of the gene which has been used in Example 3 for allelic definition by DSCA, includes intron 2. small variations in intronic sequences of HLA class I genes have been reported (39) and these will influence the mobilities of the bands where the sequences are different from the reference strand sequence. More important for DSCA analysis is the possibility of such variations in an allelic sequence that may have arisen in different haplotypes, independently of the exon recombinants. The DSCA is sufficiently sensitive to test for intra-allelic sequence variations.

Eight common and frequent caucasoid alleles from HLA-A and HLA-B loci were investigated. Locus specific amplifications were performed as in Example 3. The amplified DNA fragments were analysed under both denaturing and non-denaturing conditions using several labelled reference strands from both loci.

The numbers of alleles analysed were:
HLA-A A2 284, A1 148, A3 82, A11 52, A32 29.
HLA-B B7 114, B8 110, B44 125.

In all cases the allelic bands migrated with identical mobility indicating that there was no intra-allelic polymorphism in the samples tested (FIG. 15). It would therefore appear that the intron sequences are conserved for each allele.

References

1.—D. Weisdorf, R. Haake & B. Blazar. Risk factors for acute graft-versus-host disease in histocompatible donor bone marrow transplantation. *Transplantation* 1991: 51: 1197–1203

2.—L. A. Ochs, W. J. Miller, A. H. Filipovich, R. J. Haake, P. B. McGlave, B. R. Blazar, N. K. C. Ramsay, J. H. Kersey & D. J. Weisdorf. Predictive factors for chronic graft-versus-host disease after histocompatible sibling donor bone marrow transplantation. *Bone Marrow Transplant* 1994: 13; 455–460

3.—L. A Smyth, C. S. Witt, F. T. Christiansen, R. P. Hermann, P. N. Hollingsworth, D. C. Townend, E Edward & R. L. Dawking. The MHC influences acute graft versus host disease in MHC matched adults undergoing allogenic one marrow transplantation. *Bone Marrow Transplant* 1993: 12; 351–355

4.—A. Bacigalupo, F. Gualandi, M. T. Van Lint, M. Sessarego, F. Frassoni, D. Occhini, T. Lamparelli, R. Oneto, V. Vitale, R. Corvo, E. Raul de la Torre & A. M. Marmont. Multivariate analysis of risk factors for survival and relapse in chronic granulocytic leukaemia following allogenic marrow transplantation: impact of disease related variables (Sokal score). *Bone Marrow Transplant* 1993: 12; 443–448

5.—J. Sierra, A. Graneda, J. Garcia, A. Valls, E. Carreras, M. Rovira, C. Canals, E. Martinez, C. Punti, M. Algara, P. Martin, A. Merino, M. J. Terol, A. Urbano-Ispizua & C. Rozman. Autologous bone marrow transplantation for acute leukaemia: results and prognostic factors in 90 consecutive patients. *Bone Marrow Transplant* 1993: 12; 517–523

6.—J. L. Bidwell. Applications of the polymerase chain reaction to HLA class II typing. *Vox Sang* 1992: 63; 81–89

7.—P. Parham, E. Adams & k. L. Arnett. The Origins of HLA-A, B. C Polymorphism. *Immunological Reviews* 1995: 143; 141–180

8.—P. Krausa, M. Brywka III, D. Savage, K. M. Hui, M. Bunce, J. L. F. Ngai, D. L. T. Teo, Y. W. Ong, D. Barouch, C. E. M. Allsop, A. V. S. Hill, A. J. McMichael, J. G. Bodmer & M. J. Browning. Genetic polymorphism within HLA-A*02: significant allelic variation revealed in different populations. *Tissue Antigens* 1995: 45; 223–231

9.—P. Krausa, J. G. Bodmer, M. J. Browning. Defining the common subtypes of HLA A9, A10, A28 and A19 by use of ARMS/PCR. *Tissue Antigens* 1993: 42; 91–99

10.—C. W. Summers, V. J. Hampson & G. M. Taylor. HLA class I non-coding nucleotide sequences, 1992. *European Journal of Immunogenetics* 1993: 20; 201–240

11.—S. Hoshino, A. Kimura, Y. Fukuda, K. Dohi & T. Sasazuki. Polymerase chain reaction-single-strand conformation polymorphism analysis of polymorphism in DPA1 and DPB1 genes: A simple, economical, and rapid method for histocompatibility testing. *Human Immunology* 1992: 33; 98–107

12.—M. Orita, Y. Suzuki, T. Sekiya & K. Hayashi. Rapid and sensitive detection of point mutations and DNA polymorphisms using the polymerase chain reaction. *Genomics* 1989: 5; 874–879

13.—Y. Suzuki, T. Sekiya & K. Hayashi. Allele-specific polymerase chain reaction: A method for amplification and sequence determination of a single component among a mixture of sequence variants. *Analytical Biochemistry* 1991: 192; 82–84

14.—R. Blasczyk, U. Hahn, J. Wehling, D. Huhn & A. Salama. Complete subtyping of the HLA-A locus by sequence-specific amplification followed by direct sequencing or single-strand conformation polymorphism analysis. *Tissue Antigens*. 1995: 46; 86–95

15.—R. Blasczyk, J. Wehling, B. S. Kubens, U. Hahn, D. Huhn & A. Salama. A novel HLA-A24 allele (A*2405) identified by single-strand conformation polymorphism analysis and confirmed by solid-phase sequencing and isoelectric focusing. *Tissue Antigens* 1995: 46; 54–58

16.—M. Orita, H. Iwahana, H. Kanazawa, K. Hayashi and T. Sekiya. Detection of polymorphism of human DNA by gel electrophoresis as single-strand conformation polymorphism. *Proc Natl Acad Sci USA* 1989: 86; 2766–2770

17.—G. Fischer and L. S. Lerman. DNA fragments differing by a single base-pair substitutions are separated in denaturing gradient gels: Correspondence with melting theory. *Proc Natl Acad Sci USA* 1983: 80; 1579–1583

18.—K. Henco and M. Heibey. Quantitative PCR: the determination of template number copy numbers by temperature gradient gel electrophoresis. *Nucleic Acid Res* 1990: 18; 6733–6734

19.—T. M. Clay, J. L. Bidwell, M. R. Howard & B. A. Bradley. PCR-fingerprinting for selection of HLA matched unrelated marrow donors. *Lancet* 1991: 337; 1049–52

20.—A. Bhattacharyya & D. M. J. Lilley. The contrasting structures of mismatched DNA sequences containing looped-out bases (bulges) and multiple mismatches (bubbles). *Nucleic Acids Res* 1989: 17; 6821–6840

21.—F. Aboul-ela, D. Koh & I. Tinoco. Base-base mismatches. Thermodynamics of double helix formation for dCA3XA3G+dCT3YT3G (X, Y=A, C, G, T) *Nucleic Acids Res* 1985: 13; 4811–4824

22.—J. Y. Tong, A. Hammad, W. A. Rudert, M. Trucco & S. Hsia. Heteroduplexes for HLA DQB1 identity of family members and kidney donor-recipient pairs. *Transplantation* 1994: 57; 741–745

23.—R. Sorrentino, I. Cascino & R. Tosi. Subgrouping of DR4 alleles by DNA heteroduplex analysis. *Human Immunology* 1992: 33; 18–23

24.—M. White, M. Carvalho, D. Derse, S. O'Brien & M. Dean. Detecting single base substitutions as heteroduplex polymorphisms. *Genomics* 1992: 12; 301–306

25.—M. Carrington, M. White, M. Dean, D. Mann & F. E. Ward. The use of DNA heteroduplex patterns to map recombination, within the HLA class II region. *Human Immunology* 1992: 33; 114–121

26.—N. A. P. Wood, T. M. Clay & J. L. Bidwell. HLA-DR/Dw matching by PCR Fingerprinting: The origin of PCR fingerprints and further applications. *European Journal of Immunogenetics* 1991: 18; 147–153

27.—M. Allen, L. Liu & U. Gyllensten. A comprehensive polymerase chain reaction-oligonucleotide typing system for HLA class I A locus. *Human Immunology* 1994: 40; 25–32

28.—X. Gao, I. B. Jakobsen & S. W. Serjeantson. Characterization of the HLA-A polymorphism by locus-specific polymerase chain reaction amplification and oligonucleotide hydridization. *Human Immunology* 1994: 41; 267–279

29.—A. Selvakumar, C. B. Granja, M. Salazar, S. M. Alosco, E. J. Yunis & B. Dupont. A novel subtype of A2 (A*0217) isolated from the South American Indian B-cell line AMALA. *Tissue Antigens* 1995: 45; 343–347

30.—E. W. Petersdorf & J. A. Hansen. A comprehensive approach for typing the alleles of the HLA-B locus by automated sequencing. *Tissue Antigens* 1995: 46; 73–85

31.—N. Cereb, P. Maye, S. Lee, Y. Kong & S. Y. Yan. Locus specific amplification of HLA class I genes from genomic DNA. Tissue Antigens 1995.

32.—J Lyons. Analysis of ras gene point mutations by PCR and oligonucleotide hybridisation. In eds MA Innis et al, PCR Protocols, a guide to methods and applications.Academic Press, 1990.

33.—G E Hawes, L Struyk, P J van den Elsen. Differential usage of T cell receptor V gene segments in CD4+ and CD8+ subsets of T lymphocytes in monozygotic twins. *J Immunol* 1993: 150; 2033–2045.

34.—C Giachino, M P Rocci, G De Libero, G Oderda, N Ansaldi and N Migone. An alternative approach to the assessment of T-cell clonality in celiac disease intestinal lesions through cDNA heteroduplex analysis of T-cell receptor VJ junctions. *Human Immunology* 1994: 40; 303–311.

35.—R. Arguello, H. Avakian, J. M. Goldman and J. A. Madrigal. A novel method for simultaneous high resolution identification of HLA-A, HLA-B and HLA-Cw alleles. *Prof Natl Acad Sci USA* 1996: 93; 10961–10965

36.—B. Ezquieta, J. Molano. CF2603/4delT, a new frameshift mutation in exon 13 of the cystic fibrosis transmembrane conductance regulator (CFTR) gene. *Human Genetics* 1993: 91; 614–615

37.—L. C. Tsui. Mutations and sequence variations detected in the cystic fibrosis transmembrance conductance regulator (CFTR) gene: a report from the Cystic Fibrosis Genetic Analysis Consortium. Human *Mutation* 1992: 1; 197–203

38.—J. Zielenski, D. Bozon, B. Karem. Identification of mutations in exons 1 through 8 of the cystic fibrosis transmembrane conductance regulator (CFTR) gene. *Genomics* 1991: 10; 214–228

39.—N. Cereb, Y. Kong, S. Lee, P. Maye and S. Y. Yang. Nucleotide sequences of MHC class I introns 1, 2 and 3 in humans and intron 2 in non-human primates. *Tissue Antigens* 1996: 47; 498–511

What is claimed is:

1. A method for identifying a DNA molecule comprising:
   (a) hybridizing a single strand DNA molecule with a complementary reference DNA strand to form a test duplex;
   (b) separating the test duplex from at least one control duplex run in the same separation;
   (c) detecting the positions to which the test duplex and the at least one control duplex migrate in the separation;
   (d) assigning an exact numerical migration value to the position to which the test duplex migrates; and
   (e) identifying the DNA molecule by matching the exact migration value with a database of migration values of identified DNA molecules, wherein the database of migration values is independent of the separation.

2. The method of claim 1 wherein the complementary reference DNA strand is labeled.

3. The method of claim 1 further comprising repeating steps (a)–(e) one or more times wherein a different complementary reference strand is utilized in each repeat of steps (a)–(e) to identify the DNA molecule.

4. The method of claim 1 wherein step (b) comprises gel electrophoresis.

5. The method of claim 1 wherein the database of migration values comprises migration values of alleles of a gene selected from the group consisting of HLA, TAP, LMP, ras, non-classical HLA and Bf.

6. The method of claim 1 wherein the database of migration values comprises migration values for mammalian MHC genes.

7. The method of claim 5 wherein the alleles are selected from the group consisting of HLA alleles.

8. The method of claim 6 wherein the DNA molecule comprises a portion of an HLA gene.

9. The method of claim 1 further comprising confirming the identity of the DNA molecule by sequencing the test duplex, performing sequence specific primer amplification analysis on the test duplex or performing sequence specific oligonucleotide analysis on the test duplex.

10. The method of claim 1 wherein the method can resolve a difference of one, two or three nucleic acid positions between the DNA molecule and the complementary sequence of the complementary reference DNA strand.

11. The method of claim 1 wherein the DNA molecule and complementary reference DNA strand have the same number of nucleotides.

12. The method of claim 1 wherein the complementary reference DNA strand consists of the wild type sequence of a naturally occurring DNA strand of interest or a naturally occurring mutant thereof.

13. The method of claim 1 wherein the at least one control duplex comprises (i) duplexes which have faster and slower mobility than the test duplex or (ii) duplexes which have graded mobilities.

14. The method of claim 1 wherein the identified DNA molecule is matched to a second identified DNA molecule and the method is used to match tissue between a prospective tissue donor and a prospective tissue recipient.

15. The method of claim 1 further comprising amplifying the DNA molecule prior to step (a).

16. A method for identifying a DNA molecule, comprising:
   (a) amplifying a DNA molecule to produce amplified double stranded DNA molecules;
   (b) denaturing the amplified double stranded DNA molecules into single stranded DNA molecules wherein the single stranded DNA molecules include sense and antisense strands;
   (c) hybridizing the single stranded DNA molecules with reference DNA strands which are complementary to the single stranded DNA molecules to form test duplexes;
   (d) separating the test duplexes from at least one control duplex run in the same separation;
   (e) detecting the positions to which the test duplexes and the at least one control duplex migrate in the separation;
   (f) assigning an exact numerical migration value to the position to which the test duplex migrates; and
   (g) identifying the DNA molecule by matching the exact migration with a database of migration values of identified DNA molecules, wherein the database of migration values is independent of the separation.

17. The method of claim 16 wherein the reference DNA strands are labeled.

18. The method of claim 16 further comprising repeating steps (a)–(g) one or more times wherein a different complementary reference strand is utilized in each repeat of steps (a)–(g) to identify the DNA.

19. The method of claim 16 wherein step (f) comprises:
   (i) assigning a migration value to the at least one control duplex; and
   (ii) assigning the exact numerical migration value to the test duplex based on the relative migration position of the test duplex compared to the migration value of the control duplex.

* * * * *